(12) United States Patent
Womack et al.

(10) Patent No.: US 12,291,691 B2
(45) Date of Patent: *May 6, 2025

(54) ALKYL ENOL ETHER PROPERFUME

(71) Applicant: FIRMENICH SA, Satigny (CH)

(72) Inventors: Gary Bernard Womack, Plainsboro, NJ (US); Brinda Indradas, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 940 days.

This patent is subject to a terminal disclaimer.

(21) Appl. No.: 17/273,556

(22) PCT Filed: Dec. 19, 2019

(86) PCT No.: PCT/EP2019/086276
§ 371 (c)(1),
(2) Date: Mar. 4, 2021

(87) PCT Pub. No.: WO2020/127708
PCT Pub. Date: Jun. 25, 2020

(65) Prior Publication Data
US 2021/0340462 A1    Nov. 4, 2021

Related U.S. Application Data

(60) Provisional application No. 62/782,475, filed on Dec. 20, 2018.

(30) Foreign Application Priority Data

Jan. 3, 2019   (EP) ..................................... 19150163

(51) Int. Cl.
| | |
|---|---|
| *C11B 9/00* | (2006.01) |
| *A61K 8/33* | (2006.01) |
| *A61Q 5/02* | (2006.01) |
| *A61Q 5/12* | (2006.01) |
| *A61Q 15/00* | (2006.01) |
| *A61Q 19/10* | (2006.01) |
| *C07C 29/50* | (2006.01) |
| *C07C 43/15* | (2006.01) |
| *C07C 43/168* | (2006.01) |
| *C07C 43/215* | (2006.01) |
| *C07C 45/37* | (2006.01) |
| *C07C 67/39* | (2006.01) |
| *C11D 3/20* | (2006.01) |
| *C11D 3/50* | (2006.01) |

(52) U.S. Cl.
CPC .............. *C11B 9/0061* (2013.01); *A61K 8/33* (2013.01); *A61Q 5/02* (2013.01); *A61Q 5/12* (2013.01); *A61Q 15/00* (2013.01); *A61Q 19/10* (2013.01); *C07C 29/50* (2013.01); *C07C 43/15* (2013.01); *C07C 43/168* (2013.01); *C07C 43/215* (2013.01); *C07C 45/37* (2013.01); *C07C 67/39* (2013.01); *C11D 3/2068* (2013.01); *C11D 3/50* (2013.01); *C07C 2601/16* (2017.05); *C07C 2601/18* (2017.05)

(58) Field of Classification Search
CPC . A61Q 5/02; A61Q 5/12; A61Q 15/00; A61Q 19/10; C11D 3/2068; C11D 3/50; A61K 8/33; C07C 2601/16; C07C 45/36; C07C 45/34; C07C 45/37; C07C 43/215; C07C 43/188; C07C 43/166; C07C 43/168; C07C 43/15; C07C 63/16; C07C 29/50; C07C 67/39; C07C 49/04; C07C 47/02; C11B 9/0061
USPC ....................................................... 512/25, 1
See application file for complete search history.

(56) References Cited

U.S. PATENT DOCUMENTS

| | | | | |
|---|---|---|---|---|
| 3,928,419 | A * | 12/1975 | Light .................... | A23L 27/204 560/70 |
| 11,667,869 | B2 * | 6/2023 | Womack ................. | A61K 8/33 512/21 |
| 2002/0193269 | A1 * | 12/2002 | Anderson ............ | C11D 3/2093 510/266 |
| 2004/0013779 | A1 | 1/2004 | Mookherjee et al. | |
| 2016/0122271 | A1 * | 5/2016 | Indradas ............... | C11B 9/0061 568/426 |
| 2018/0016521 | A1 | 1/2018 | Indradas et al. | |

FOREIGN PATENT DOCUMENTS

| | | |
|---|---|---|
| CN | 105143163 A | 12/2015 |
| CN | 107530297 A | 1/2018 |
| DE | 2336980 A1 | 2/1975 |
| DE | 102014226194 A1 | 6/2016 |
| EP | 0998911 A2 | 5/2000 |

(Continued)

OTHER PUBLICATIONS

International Search Report and Written Opinion for corresponding PCT/EP2019/086276 mailed Feb. 14, 2020, 15 pages.

(Continued)

*Primary Examiner* — Jessica Whiteley
(74) *Attorney, Agent, or Firm* — Armstrong Teasdale LLP

(57) ABSTRACT

Described herein are compounds of formula (I) as properfume compounds. In particular, described herein is a method to release a compound being a ketone of formula (II), a formate ester of formula (III), and/or an alcohol of formula (IV) by exposing the compound of formula (I) to an environment wherein it is oxidized. Moreover, a perfuming composition and a perfumed consumer product including at least one compound of formula (I) are also described.

7 Claims, 1 Drawing Sheet

(56) References Cited

FOREIGN PATENT DOCUMENTS

| WO | 20100029462 A1 | | 3/2010 | |
|---|---|---|---|---|
| WO | WO-2010029462 A1 | * | 3/2010 | ............... A61K 8/33 |
| WO | 2014180791 A1 | | 11/2014 | |

OTHER PUBLICATIONS

Bône et al. Chimia, 2011, vol. 65, n° 3, 177-181.
Lee H Y J Microencapsulation 2002 19(5) 559-569.
Arctander n° 2200 & 2575, Perfume and Flavor Chemical, 1969, Montclair, NJ, USA.
Dietrich et al., Acta Polymerica, 41 (1990), n° 2, 91-95.
Dietrich et al., Acta Polymerica, 40 (1989), n° 4, 243-251.
Dietrich et al., Acta Polymerica, 40 (1989), n° 11, 683-690.
Dietrich et al., Acta Polymerica, 40 (1989), n° 5, 325-331.
E.J. Corey et al., J. of Organic Chemistry, 1978, vol. 43, No. 17, 3418-3420.
Kanno et al., "Oxygenation of Aromatic Vinyl Ethers. A Noticeable Formation of Epoxides and Reaction Mechanism", Bulletin of the Chemical Society of Japan, 1981, pp. 2330-2336, 54(8).
Tokunaga et al., "Copper-catalyzed oxidative cleavage of carbon-carbon double bond of enol ethers with molecular oxygen", Journal of Organometallic Chemistry, 2005, pp. 5378-5382, 690(23).

* cited by examiner

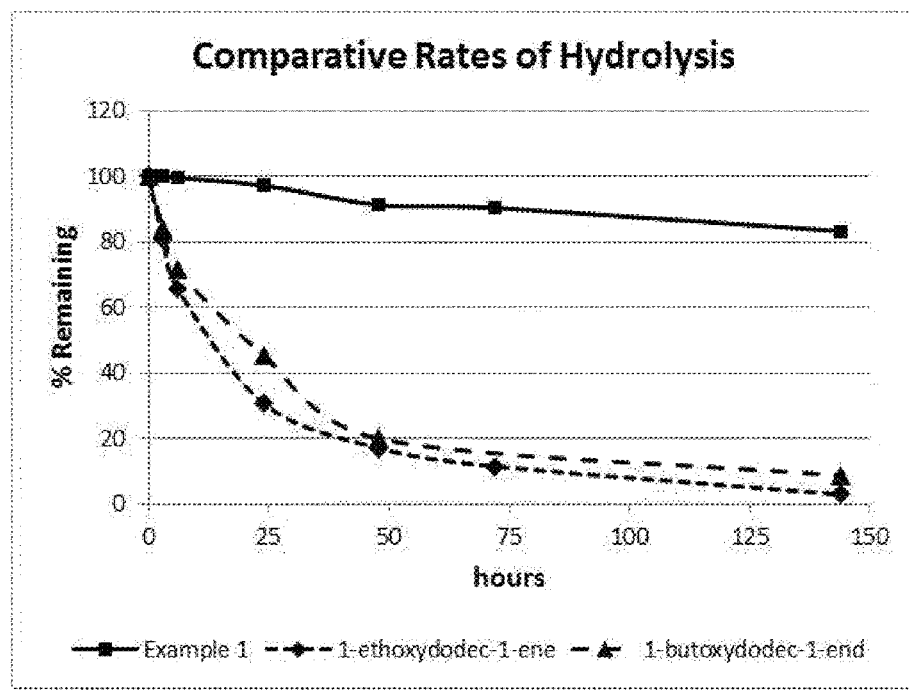

ALKYL ENOL ETHER PROPERFUME

CROSS-REFERENCE TO RELATED APPLICATIONS

This application is a U.S. National Phase Application of International Patent Application No. PCT/EP2019/086276, filed Dec. 19, 2019, which claims the benefit of priority to U.S. Provisional Patent Application No. 62/782,475, filed Dec. 2, 2018, and to European Patent Application No. 19150163.4, filed Jan. 3, 2019, the entire contents of each of which are hereby incorporated by reference herein.

TECHNICAL FIELD

The present invention relates to compounds of formula (I) as properfume compounds. In particular, the present invention relates to a method to release a compound being a ketone of formula (II), a formate ester of formula (III) and/or an alcohol of formula (IV), by exposing the compound of formula (I) to an environment wherein it is oxidized. Moreover, the present invention relates to a perfuming composition and a perfume consumer product comprising at least one compound of formula (I).

BACKGROUND

The perfume industry has a particular interest for compositions or additives which are capable of prolonging or enhancing the perfuming effect of a mixture of several fragrances at the same time over a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients are unstable and need to be protected against slow degradation prior to their use. Long-lasting perfumes are desirable for various applications, as for example fine or functional perfumery or cosmetic preparations. The washing and softening of textiles is a particular field in which there is a constant need to enable the effect of active substances, in particular perfumes, or perfuming compositions, to be effective for a certain period of time after washing, softening and drying. Indeed, many active substances which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

It has now been surprisingly found that alkyl enol ether compounds according to the present invention solve the above-mentioned problems and are capable of efficiently releasing a compound being a ketone of formula (II), a formate ester of formula (III) and/or an alcohol of formula (IV) while being stable in consumer product.

BRIEF DESCRIPTION OF THE DRAWING

FIG. 1: Analysis of the concentration of (2-((2-methylundec-1-en-1-yl)oxy)ethyl)benzene, 1-ethoxydodec-1-ene and 1-butoxydodec-1-ene in an acidic solution as a function of time.

DETAILED DESCRIPTION

Olfaction is a complex and dynamic process, and controlling the release profile of volatile fragrance compounds may maximize the impact of fragrance formulations and enrich the sensorial experience. Profragrances, such as the compounds of the present invention add a dimension of control and long-lastingness to the release profile of highly volatile perfumery raw materials (PRMs).

Without intending to be limited to any particular theory, the compounds of the present invention may achieve their effect on the olfactive properties of a perfuming composition by tethering the PRM to a molecular anchor and requiring a specific reaction mechanism under certain environmental conditions to release the volatile PRM from this anchor. In the present invention, the release of one, two or up to three PRMs is prompted by oxidation when the profragrance is exposed to the oxygen in ambient air.

In a first aspect, the present invention relates to a method to release from a precursor compound, compounds selected from the group consisting of
a) a ketone of formula

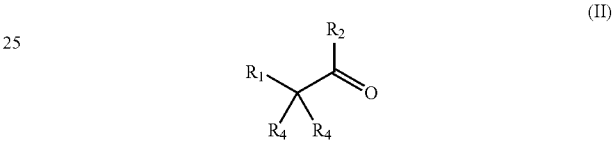

(II)

wherein $R_1$ represents a $C_{1-15}$ alkyl, $C_{2-15}$ alkenyl, $C_{3-15}$ cycloalkyl, $C_{5-15}$ cycloalkenyl or $C_{6-10}$ aryl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R_2$ represents a $C_{1-15}$ alkyl group;

$R_1$ and $R_2$, when taken together, form a $C_{5-15}$ cycloalkyl, $C_{5-15}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid, 4-methylcyclohex-3-en-1-yl and/or $C_{1-4}$ carboxylic ester group, wherein the heteroatom represents one or more of an oxygen;

$R_4$, each independently, represent a hydrogen or a $C_{1-5}$ alkyl group; and $R_1$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

b) a formate ester of formula

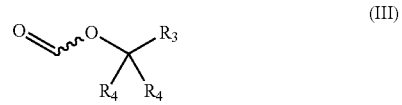

(III)

wherein $R_3$ represents a hydrogen, a $C_{1-15}$ alkyl, $C_{2-15}$ alkenyl, $C_{3-15}$ cycloalkyl or $C_{5-15}$ cycloalkenyl group, each optionally substituted with one or more a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and $R_4$ has the same meaning as defined above; and $R_3$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

c) an alcohol of formula

wherein $R_3$ and $R_4$ have the same meaning as defined above;

wherein at least one of the compounds of formula (II), (III) or (IV) is an active compound;

wherein the precursor compound comprises a compound of formula (I)

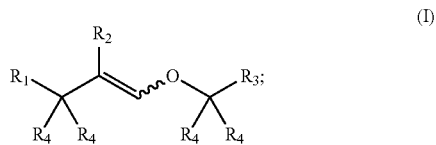

wherein $R_1$; $R_2$, $R_3$ and $R_4$ have the same meaning as defined above;

by exposing the precursor compound of formula (I) to an environment wherein the compound is oxidized; i.e. ambient conditions.

The terms "active compound", "active volatile compound", "active volatile ketone, formate ester and/or alcohol" or the similar, are understood as ketone, formate ester and/or alcohol compounds being capable of bringing a benefit or effect into its surrounding environment. In particular the "active compound" is selected from the group consisting of a perfuming ingredient, flavoring ingredient, malodor counteracting ingredient and insect repellent or attractant ingredient. Therefore, to be considered as an "active compound" the compound has to possess at least one property which renders it useful as a perfuming ingredient, as a malodor counteracting ingredient, a flavoring ingredient, and/or as an insect repellent or attractant.

The term "perfuming ingredient" is understood as a compound which is used as an active ingredient in perfuming preparations or compositions in order to impart a hedonic effect. In other words, a compound to be considered as being a perfuming ingredient, must be recognized by a skilled person in the art of perfumery as being able to impart or modify in a positive or pleasant way the odor of a composition, and not just as having an odor. The term "flavoring ingredient" is understood to as being capable of imparting a taste sensation to the taster's pallet. The term "malodor counteracting ingredient" is understood as being capable of reducing the perception of malodor, i.e. of an odor that is unpleasant or offensive to the human nose. The term "insect attractant or repellent" is understood as a compound having a positive or negative effect on insects. Examples of insect attractant or repellent ingredients can be found in reference texts or in other works of a similar nature as for example: A. M. El-Sayed, The Pherobase 2005, http://www.pherobase.net.

According to the above and below mentioned embodiments of the invention, the method according to the present invention is particularly useful when the active compound is a perfuming ingredient, i.e. a perfuming ketone, formate ester and/or alcohol. A "perfuming ketone, formate ester and/or alcohol" is a compound, which is of use in the perfumery industry, i.e. a compound which is used as active ingredient in perfuming preparations or compositions in order to impart a hedonic effect. In other words, such a ketone, formate ester and/or alcohol, to be considered as being a perfuming one, must be recognized by a person skilled in the art of perfumery as being able to impart or modify in a positive or pleasant way the odor of a composition, and not just as having an odor. The perfuming ketone, formate ester and/or alcohol can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

Herein described, the terms "perfuming ketone, formate ester and/or alcohol" are also referred to as "perfuming compounds".

Practically, the invention is carried out exactly in the same manner, independently of the exact properties of the active ketone, formate ester or alcohol. Therefore, it is understood that, even if the invention will be further illustrated herein below with a specific reference to "perfuming compounds", the below embodiments are also applicable to other active ketone, formate ester and/or alcohol (i.e. it is possible to replace the expression "perfuming" with "flavoring", "malodor counteracting", "insect attractant" or with "insect repellent" for instance).

The term "optionally" is understood that a certain group to be optionally substituted can or cannot be substituted with a certain functional group. The term "one or more" is understood as being substituted with 1 to 7, preferably 1 to 5 and more preferably 1 to 3 of a certain functional group.

The terms "alkyl" and "alkenyl" are understood as comprising branched and linear alkyl and alkenyl groups. The terms "alkenyl", "cycloalkenyl" and "heterocycloalkenyl" is understood as comprising 1, 2 or 3 olefinic double bonds, preferably 1 or 2 olefinic double bonds. The terms "cycloalkyl", "cycloalkenyl", "heterocycloalkyl" and "heterocycloalkenyl" are understood as comprising a monocyclic or fused, spiro and/or bridged bicyclic or tricyclic cycloalkyl, cycloalkenyl, heterocycloalkyl and heterocycloalkenyl groups, preferably monocyclic cycloalkyl, cycloalkenyl, heterocycloalkyl and heterocycloalkenyl groups.

The term "aryl" are understood as comprising any group comprising at least one aromatic group such as phenyl, indenyl, indanyl, tetrahydronaphthalenyl or naphthalenyl group.

The term "$C_{1-15}$ alkoxy" is understood as a RO— group wherein R is a $C_{1-15}$ alkyl or alkenyl group being linear, branched, cyclic or aliphatic.

According to any one of the above embodiments of the invention, said compounds (I) are $C_{16}$-$C_{28}$ compounds, particularly $C_{18}$-$C_{26}$ compounds, even more particularly $C_{19}$-$C_{24}$ compounds.

In a preferred embodiment, in case, "$R_1$ and $R_4$, when taken together" and/or "$R_3$ and $R_4$, when taken together" form a cycloalkenyl group, it is understood that the olefinic double bond is not adjacent to the carbon connecting $R_1$ and $R_4$ or $R_3$ and $R_4$, respectively. In a preferred embodiment, in case an alkenyl group is substituted with an alkoxy group, the alkoxy group cannot be adjacent to the olefinic double bond of the alkenyl group to form an enol ether.

According to any embodiments of the invention, $R_1$ represents a $C_{1-10}$ alkyl, $C_{2-10}$ alkenyl, $C_{3-11}$ cycloalkyl or $C_{5-11}$ cycloalkenyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-4}$ alkyl or a $C_{1-4}$ alkoxy, carboxylic acid and/or $C_{1-4}$ carboxylic ester group.

According to any embodiments, $R_1$ represents a $C_{1-10}$ alkyl, $C_{2-10}$ alkenyl or $C_{3-11}$ cycloalkyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-4}$ alkyl or a $C_{1-4}$ alkoxy group.

According to any embodiments, $R_1$ represents a $C_{1-10}$ alkyl group, optionally substituted with a $C_{5-7}$ cycloalkyl, $C_{5-7}$ cycloalkenyl and/or $C_6$ aryl group, each optionally substituted with one or more of a $C_{1-4}$ alkyl and/or $C_{1-4}$ alkoxy group. Preferably, $R_1$ represents a $C_{1-10}$ alkyl group, optionally substituted with a $C_{5-7}$ cycloalkyl, $C_{5-7}$ cycloalkenyl and/or $C_6$ aryl group, each optionally substituted with one or more of methyl and/or methoxy group.

According to any embodiments, $R_2$ represents a $C_{1-10}$ alkyl group. In a particular embodiment, $R_2$ represents a $C_{1-5}$ alkyl group. In a particular embodiment, $R_2$ represents a $C_{1-3}$ alkyl group, preferably a methyl group or an ethyl group.

According to any embodiments, $R_1$ and $R_2$, when taken together, form a $C_{5-15}$ cycloalkyl, $C_{5-15}$ cycloalkenyl, $C_{4-15}$ heterocycloalkyl or $C_{4-15}$ heterocycloalkenyl group, each optionally substituted with one or more of a $C_{1-7}$ alkyl, $C_{2-8}$ alkenyl, $C_{1-5}$ alkoxy, $C_{3-8}$ cycloalkyl, $C_{5-8}$ cycloalkenyl or $C_6$ aryl group, each optionally substituted with one or more of a $C_{1-5}$ alkyl, $C_{1-5}$ alkoxy, carboxylic acid, 4-methylcyclohex-3-en-1-yl and/or $C_{1-4}$ carboxylic ester group, wherein the heteroatom represents one or more of an oxygen.

According a particular embodiment, $R_1$ and $R_2$, when taken together, form a $C_{5-15}$ cycloalkyl or $C_{5-15}$ cycloalkenyl group, each optionally substituted with one to 4 of a $C_{1-7}$ alkyl or $C_{2-8}$ alkenyl group.

According to any embodiments, $R_1$ and $R_2$, when taken together, form a $C_{5-11}$ cycloalkyl, $C_{5-11}$ cycloalkenyl, $C_{4-11}$ heterocycloalkyl or $C_{4-11}$ heterocycloalkenyl group, each optionally substituted with one or more of a $C_{1-7}$ alkyl, $C_{2-8}$ alkenyl $C_{1-5}$ alkoxy, $C_{3-8}$ cycloalkyl, $C_{5-8}$ cycloalkenyl or $C_6$ aryl group, each optionally substituted with one or more of a $C_{1-5}$ alkyl, $C_{1-5}$ alkoxy, carboxylic acid, 4-methylcyclohex-3-en-1-yl and/or $C_{1-4}$ carboxylic ester group, wherein the heteroatom represents one or more of an oxygen.

In a particular embodiment, $R_1$ and $R_2$, when taken together, form a $C_{5-11}$ cycloalkyl, $C_{5-11}$ cycloalkenyl, $C_{4-11}$ heterocycloalkyl or $C_{4-11}$ heterocycloalkenyl group, each optionally substituted with one or more of a $C_{1-5}$ alkyl, $C_{1-5}$ alkoxy, $C_{3-8}$ cycloalkyl, $C_{5-8}$ cycloalkenyl or $C_6$ aryl group, each optionally substituted with one or more of a $C_{1-5}$ alkyl, $C_{1-5}$ alkoxy, carboxylic acid and/or $C_{1-4}$ carboxylic ester group, wherein the heteroatom represents one or more of an oxygen.

According to any embodiments, $R_1$ and $R_2$, when taken together, form a $C_{5-7}$ cycloalkyl, $C_{5-7}$ cycloalkenyl, $C_{5-7}$ heterocycloalkyl or $C_{5-8}$ heterocycloalkenyl group, each optionally substituted with one or more of a $C_{1-7}$ alkyl, $C_{2-6}$ alkenyl, $C_{1-4}$ alkoxy, $C_{5-7}$ cycloalkyl, $C_{5-7}$ cycloalkenyl or $C_6$ aryl group, each optionally substituted with one or more of a $C_{1-3}$ alkyl, $C_{1-3}$ alkoxy, carboxylic acid, 4-methylcyclohex-3-en-1-yl and/or $C_{1-3}$ carboxylic ester group, wherein the heteroatom represents one or more of an oxygen.

In a particular embodiment, $R_1$ and $R_2$, when taken together, form a $C_{5-7}$ cycloalkyl, $C_{5-7}$ cycloalkenyl, $C_{5-7}$ heterocycloalkyl or $C_{5-8}$ heterocycloalkenyl group, each optionally substituted with one or more of a $C_{1-4}$ alkyl, $C_{1-4}$ alkoxy, $C_{5-7}$ cycloalkyl, $C_{5-7}$ cycloalkenyl or $C_6$ aryl group, each optionally substituted with one or more of a $C_{1-3}$ alkyl, $C_{1-3}$ alkoxy, carboxylic acid and/or $C_{1-3}$ carboxylic ester group, wherein the heteroatom represents one or more of an oxygen.

According to any embodiments, $R_1$ and $R_2$, when taken together, form a $C_{5-7}$ cycloalkyl or $C_{5-7}$ cycloalkenyl group, each optionally substituted with one or more of a $C_{1-7}$ alkyl, $C_{2-6}$ alkenyl group or or $C_{1-4}$ alkoxy group.

According to any embodiments, $R_1$ and $R_2$, when taken together, form a $C_{5-7}$ cycloalkyl or $C_{5-7}$ cycloalkenyl group, each optionally substituted with one or more of a $C_{1-4}$ alkyl, $C_{2-6}$ alkenyl or $C_{1-4}$ alkoxy group.

According to any embodiments, $R_1$ and $R_2$, when taken together, form a a $C_{10-15}$ cycloalkyl or $C_{10-15}$ cycloalkenyl group, each optionally substituted with one methyl group or $R_1$ and $R_2$, when taken together, form a $C_{5-6}$ cycloalkyl or $C_{5-6}$ cycloalkenyl group, each optionally substituted with one to three of a $C_{1-7}$ alkyl, $C_{2-6}$ alkenyl or $C_{1-4}$ alkoxy group.

According to any embodiments, $R_4$, each independently, represent a hydrogen atom or a $C_{1-5}$ alkyl group. In a particular embodiment, $R_4$, each independently, represent a hydrogen atom or a $C_{1-3}$ alkyl group. In a particular embodiment, $R_4$, each independently, represent hydrogen atom and only one $R_4$ represents a $C_{1-3}$ alkyl group. In a particular embodiment $R_4$, each independently represent hydrogen atom and only one $R_4$ represents a $C_{1-2}$ alkyl group. In a preferred embodiment, each $R_4$ represents hydrogen atom.

According to any embodiments, $R_1$ and $R_4$, being adjacent to $R_1$; when taken together, form a $C_{3-11}$ cycloalkyl or $C_{5-11}$ cycloalkenyl group, each optionally substituted with one or more of a $C_{1-5}$ alkyl, $C_{1-5}$ alkoxy, $C_{3-7}$ cycloalkyl, $C_{5-7}$ cycloalkenyl and/or $C_6$ aryl group, each optionally substituted with one or more of a $C_{1-4}$ alkyl or $C_{1-4}$ alkoxy group.

According to any embodiments, $R_1$ and $R_4$, when taken together, form a $C_{3-11}$ cycloalkyl or $C_{5-11}$ cycloalkenyl group, each optionally substituted with one or more of a $C_{1-3}$ alkyl or $C_{1-3}$ alkoxy group.

According to any embodiments, $R_1$ and $R_4$, when taken together, form a $C_{3-11}$ cycloalkyl group, optionally substituted with one or more of a $C_{1-3}$ alkyl or $C_{1-3}$ alkoxy group.

According to any embodiments, $R_3$ represents a $C_{1-10}$ alkyl, $C_{2-10}$ alkenyl, $C_{3-15}$ cycloalkyl or $C_{5-11}$ cycloalkenyl group, each optionally substituted with one or more of a $C_{1-5}$ alkyl, $C_{1-5}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-5}$ alkyl or $C_{1-5}$ alkoxy group.

According to any embodiments, $R_3$ represents a $C_{1-10}$ alkyl, $C_{3-10}$ alkenyl, $C_{4-15}$ cycloalkyl or $C_{5-11}$ cycloalkenyl group, each optionally substituted with one or more of a $C_{1-4}$ alkyl, $C_{1-4}$ alkoxy, $C_{5-6}$ cycloalkyl, $C_{5-6}$ cycloalkenyl $C_6$ aryl and/or $C_6$ aryloxy group, each optionally substituted with one or more of a $C_{1-3}$ alkyl or $C_{1-3}$ alkoxy group.

According to any embodiments, $R_3$ represents a $C_{1-10}$ alkyl, $C_{3-10}$ alkenyl or $C_{5-15}$ cycloalkyl group, each optionally substituted with one or more of a $C_{1-4}$ alkyl, $C_6$ aryl and/or $C_6$ aryloxy group.

According to any embodiments, $R_3$ represents a benzyl, phenoxymethyl, heptyl, pentyl, 4-methylhex-5-en-1-yl or pent-5-en-1-yl group.

According to any embodiments, $R_3$ and $R_4$, being adjacent to $R_3$, when taken together, form a $C_{3-12}$ cycloalkyl or $C_{5-11}$ cycloalkenyl group, each optionally substituted with one or more of a $C_{1-5}$ alkyl, $C_{1-5}$ alkoxy, $C_{3-7}$ cycloalkyl, $C_{5-7}$ cycloalkenyl and/or $C_6$ aryl group, each optionally substituted with one or more of a $C_{1-4}$ alkyl or $C_{1-4}$ alkoxy group.

According to any embodiments, $R_3$ and $R_4$, when taken together, form a $C_{3-12}$ cycloalkyl or $C_{5-11}$ cycloalkenyl group, each optionally substituted with one or more of a $C_{1-3}$ alkyl or $C_{1-3}$ alkoxy group.

According to any embodiments, $R_3$ and $R_4$, when taken together, form a $C_{3-12}$ cycloalkyl group, optionally substituted with one or more of a $C_{1-3}$ alkyl or $C_{1-3}$ alkoxy group.

In a particular embodiment, the ketone of formula (II), the formate ester of formula (III) and/or the active alcohol of formula (IV) are perfuming ingredients. For a person skilled in the art it is also evident that compounds according to the present invention are inherently volatile compounds.

The ketone, formate ester and/or alcohol may be advantageously characterized by a vapor pressure above 1.0 Pa, as obtained by calculation using the software EPIwin v. 3.10 (2000, available at the US Environmental Protection Agency). According to another embodiment, the vapor pressure of the ketone, formate ester and/or alcohol may be above 5.0, or even above 7.0 Pa.

In a preferred embodiment, the compound of formula (I) is non-volatile. The compound of formula (I) may be advantageously characterized by a vapor pressure below 0.01 Pa, as obtained by calculation using the software EPIwin v. 3.10 (2000, available at the US Environmental Protection Agency). According to a preferred embodiment, the vapor pressure is below 0.001 Pa.

In a particular embodiment, the ketone of formula (II) is selected from the group consisting of 2-butanone, 2-pentanone, 2-hexanone, 2-heptanone, 2-octanone, 2-nonanone, 2-undecanone, 2-tridecanone, 2-pentadecanone, 3-heptanone, 3-octanone, 4-nonanone, 5-undecanone, 5-methyl-3-heptanone, 6-methyl-5-hepten-2-one, 2,6-dimethyl-7-octen-4-one (dihydrotagetone), 2-(sec-butyl)cyclohexan-1-one, 2-(tert-butyl)cyclohexan-1-one, 4-(tert-butyl)cyclohexan-1-one, 4-(tert-pentyl)cyclohexan-1-one, 5-isopropyl-2-methylcyclohexan-1-one, 2-isopropyl-5-methylcyclohexan-1-one, 2,2,6-trimethylcyclohexan-1-one, 2,2,4-trimethylbicyclo[3.1.1]heptan-3-one, thujanone, 2-ethyl-4,4-dimethylcyclohexan-1-one, 1,7,7-trimethylbicyclo[2.2.1]heptan-2-one, 7-methyloctahydro-1,4-methanonaphthalen-6(2H)-one, thujopsan-4-one, 1,3,3-trimethylbicyclo[2.2.1]heptan-2-one, 4-phenyl-2-butanone, 4-(4-hydroxyphenyl)-2-butanone, 4-(4-methoxyphenyl)-2-butanone, zingerone, 4-(1,3-benzodioxol-5-yl)-2-butanone, 2-cyclohexyl-4-methyl-2-pentanone, 1-(4-methyl-1-phenoxy)-2-propanone, 2,2,6-trimethylcyclohexanone, 4-(2,6,6-trimethylcyclohex-2-en-1-yl)butan-2-one (dihydro-alpha-ionone), 4-(2,6,6-trimethylcyclohex-1-en-1-yl)butan-2-one (dihydro-beta-ionone), (5-E/Z)-6,10-dimethylundeca-5,9-dien-2-one, cycloheptadecanone, (Z)-cycloheptadec-9-en-1-one, 3-methylcyclopentadecan-1-one, (Z)-cyclopentadec-4-en-1-one, 3-methylcyclopentadec-5-en-1-one, (4E/Z,8E/Z)-cyclododeca-4,8-dien-1-one, 7-methyl-2H-benzo[b][1,4]dioxepin-3(4H)-one, 7-propyl-2H-benzo[b][1,4]dioxepin-3(4H)-one, 1-(5-propylbenzo[d][1,3]dioxol-2-yl)ethan-1-one, 4,4a,6,7,8,8a-hexahydro-1,4-methanonaphthalen-5(1H)-one, 2-pentylcyclopentan-1-one, 2-heptylcyclopentan-1-one, 2-(hex-5-en-1-yl)cyclopentan-1-one, 2,2,5-trimethyl-5-pentylcyclopentan-1-one, methyl 2-(3-oxo-2-pentylcyclopentyl)acetate, Iso-E-Super, methyl jasmonate, 1-(5-isopropyl-2-methylcyclohex-2-en-1-yl)propan-1-one, 2,2,7,9-tetramethylspiro[5.5]undec-7-en-1-one), 4-ethyl-8-methyloctahydronaphthalen-1(2H)-one, iso-longifolanone, 1-(3,3-dimethylcyclohexyl)ethan-1-one, 2,6,6-trimethylcycloheptan-1-one, 3,6,8,8-tetramethylhexahydro-1H-3a,7-methanoazulen-5(4H)-one and 2-(2-(4-methylcyclohex-3-en-1-yl)propyl)cyclopentan-1-one.

In a more particular embodiment, the ketone of formula (II) is selected from the group consisting of cyclododeca-4,8-dien-1-one, 2-(2-(4-methylcyclohex-3-en-1-yl)propyl)cyclopentan-1-one, 2-isopropyl-5-methylcyclohexan-1-one, 7-methyloctahydro-1,4-methanonaphthalen-6(2H)-one, 2-(hex-5-en-1-yl)cyclopentan-1-one, 2-ethyl-4,4-dimethylcyclohexan-1-one, 2-nonanone, 2-decanone, 2-undecanone, 4-phenyl-2-butanone, 4-(4-methoxyphenyl)-2-butanone, 4-(tert-pentyl)cyclohexan-1-one, 4-(1,3-benzodioxol-5-yl)-2-butanone, 4-(2,6,6-trimethylcyclohex-2-en-1-yl)butan-2-one (dihydro-alpha-ionone), 4-(2,6,6-trimethylcyclohex-1-en-1-yl)butan-2-one, 2-pentylcyclopentan-1-one, 2-heptylcyclopentan-1-one, 3-methylcyclopentadecan-1-one, cyclopentadecanone and 2,2,6-trimethylcyclohexanone.

In a particular embodiment, the formate ester of formula (III) are selected from the group consisting of methyl formate, ethyl formate, propyl formate, isopropyl formate, butyl formate, pentyl formate, 2-methylbutyl formate, 3-methylbutyl formate, butan-2-yl formate, 2-methylpropyl formate, cyclohexyl formate, hexyl formate, heptyl formate, octyl formate, nonyl formate, decyl formate, 3-octyl formate, benzyl formate, 3,7-dimethyloct-6-enyl formate, 3,7-dimethyloct-7-enyl formate, cinnamyl formate, 4-methoxybenzyl formate, (E)-3,7-dimethylocta-2,6-dien-1-yl formate, (Z)-3,7-dimethylocta-2,6-dien-1-yl formate, 2-hexenyl formate, 3-hexenyl formate, 3,5,5-trimethylhexyl formate, 2-phenylethyl formate, 2-(phenoxy)ethyl formate, 3-phenylpropyl formate, 3-methylbut-2-enyl formate, bornyl formate, isobornyl formate, 2-methyl-5-(prop-1-en-2-yl)cyclohex-2-en-1-yl formate, cedryl formate, cyclododecayl formate, decahydronaphthalen-2-yl formate, menthyl formate, 1-phenylethyl formate, 5-methyl-2-(prop-1-en-2-yl)cyclohexyl formate, 3a,4,5,6,7,7a-hexahydro-1H-4,7-methanoinden-5-yl formate, 3a,4,5,6,7,7a-hexahydro-1H-4,7-methanoinden-6-yl formate, 1-(3,3-dimethylcyclohexyl)ethyl formate, 2-methyl-1-phenylpropan-2-yl formate, 3,7-dimethylocta-1,6-dien-3-yl formate, 2,6-dimethyloct-7-en-2-ol formate 1-((2-(tert-butyl)cyclohexyl)oxy)butan-2-yl formate.

In a more particular embodiment, the formate ester of formula (III) is selected from the group consisting of 2-phenylethyl formate, 3-hexenyl formate, octyl formate, decyl formate, 3,7-dimethyloct-6-en-1-yl formate, 3,7-dimethyloct-7-enyl formate, 2-phenoxyethyl formate, 1-((1RS,6SR)-2,2,6-trimethylcyclohexyl)hexan-3-yl formate, hexyl formate, benzyl formate, octan-3-yl formate, (1RS,2SR,5RS)-2-isopropyl-5-methylcyclohexyl formate, cyclododecayl formate, 1-(3,3-dimethylcyclohexyl)ethyl formate, 1-((2-(tert-butyl)cyclohexyl)oxy)butan-2-yl formate, 2,6-dimethyloct-7-en-2-yl formate, 3,7-dimethyloctan-3-yl formate, 2-methyl-1-phenylpropan-2-yl formate, 2,6-dimethylheptan-2-yl formate.

In a particular embodiment, the alcohol of formula (IV) is selected from the group consisting of methanol, ethanol, propanol, isopropanol, butanol, pentanol, 2-methylbutanol, 3-methylbutanol, butan-2-ol, 2-methylpropanol, cyclohexanol, hexanol, heptanol, octanol, nonanol, decanol, 2-hexanol, 3-octanol, benzyl alcohol, 9-decen-1-ol, 3,7-dimethyloct-6-en-1-ol, 3,7-dimethyloct-7-en-1-ol, cinnamyl alcohol, 4-methoxybenzyl alcohol, (E)-3,7-dimethylocta-2,6-dien-1-ol, (Z)-3,7-dimethylocta-2,6-dien-1-ol, 2-hexen-1-ol, 3-hexen-1-ol), 3,5,5-trimethylhexanol, 2-phenylethanol, 2-(phenoxy)ethanol, 3-phenylpropanol, 2-phenylpropan-1-ol, 1-phenylethan-1-ol, 4-phenylbutan-2-ol, 3-methylbut-2-en-1-ol, (Z)-6-nonen-1-ol, borneol, isoborneol, 2-methyl-5-(prop-1-en-2-yl)cyclohex-2-en-1-ol, cedrol, cyclododecanol, decahydronaphthalen-2-ol, menthol, 1-phenylethanol, 5-methyl-2-(prop-1-en-2-yl)cyclohex-1-ol, 3-methyl-5-phenylpentan-1-ol, (4-isopropylcyclohexyl) methanol, (E)-4-methyl-3-decen-5-ol, 2-pentyl-1-cyclopentanol, 5-ethyl-2-nonanol, 4-(tert-butyl)cyclohexan-1-ol, 2-methoxy-4-propylcyclohexan-1-ol, 3a,4,5,6,7,7a-hexahydro-1H-4,7-methanoinden-5-ol, 3a,4,5,6,7,7a-hexahydro-1H-4,7-methanoinden-6-ol, 1-(3,3-dimethylcyclohexyl) ethanol, 2-methyl-1-phenylpropan-2-ol, 3,7-dimethylocta-1,6-dien-3-ol, 2,6-dimethyloct-7-en-2-ol, 2,6-dimethyloctan-2-ol, 4-cyclohexyl-2-methyl-2-butanol, (2,5-dimethyl-2,3-dihydro-1H-inden-2-yl)methanol, 1-((2-(tert-butyl) cyclohexyl)oxy)butan-2-ol, 1-((1RS,6SR)-2,2,6-trimethylcyclohexyl)hexan-3-ol, 2,6-dimethyl-2-heptanol, 2-methyl-4-[(1R)-2,2,3-trimethyl-3-cyclopenten-1-yl]-4-penten-1-ol, 2-methyl-1-phenylpropan-2-ol.
In a more preferred embodiment, the alcohol of formula (IV) is selected from the group consisting of 1-hexanol, 1-heptanol, 1-octanol, 1-nonanol, 3-octanol, 1-decanol, benzyl alcohol, 3,7-dimethyloct-6-en-1-ol, 3,7-dimethyloct-7-en-1-ol, 3-hexen-1-ol, 2-phenylethanol, 2-(phenoxy)ethanol, 9-decen-1-ol, 2,6-dimethyloct-7-en-2-ol, (2,5-dimethyl-2,3-dihydro-1H-inden-2-yl)methanol, 3-hexen-1-ol and cyclododecanol.

According to any embodiments, the compound of formula (I) is selected from the group consisting of (2-((2-methylundec-1-en-1-yl)oxy)ethyl)benzene, (2-((2-methylundec-1-en-1-yl)oxy)ethoxy)benzene, (3-methyl-4-phenethoxybut-3-en-1-yl)benzene, 1-methoxy-4-(2-methyl-3-phenethoxyallyl)benzene, (2-((2-methyl-4-(2,6,6-trimethylcyclohex-1-en-1-yl)but-1-en-1-yl)oxy)ethyl) benzene, (2-((2,2,6-trimethylcyclohexylidene)methoxy) ethyl)benzene, 2-methyl-1-(octyloxy)undec-1-ene, (3-methyl-4-(octyloxy)but-3-en-1-yl)benzene, 1-methoxy-4-(3-methyl-4-phenethoxybut-3-en-1-yl)benzene, 2-methyl-1-(octan-3-yloxy)undec-1-ene, (3-methyl-4-(octan-3-yloxy)but-3-en-1-yl)benzene, 1-methoxy-4-(2-methyl-3-(octan-3-yloxy)allyl)benzene, 1,3,3-trimethyl-2-(3-methyl-4-(octan-3-yloxy)but-3-en-1-yl)cyclohex-1-ene, ((2-methylundec-1-en-1-yl)oxy)cyclododecane, 1-((2,6-dimethyloct-7-en-2-yl) oxy)-2-methylundec-1-ene, 1-(((Z)-hex-3-en-1-yl)oxy)-2-methylundec-1-ene, (2-((2-methyldec-1-en-1-yl)oxy)ethyl) benzene, 1-((3,7-dimethyloct-6-en-1-yl)oxy)-2-methylundec-1-ene, (2-((2-ethylhex-1-en-1-yl)oxy)ethyl) benzene, (phenethoxymethylene)cyclopentadecane, (2-((4-(tert-pentyl)cyclohexylidene)methoxy)ethyl)benzene, 9-(phenethoxymethylene)cyclododeca-1,5-diene, (1 SR,4RS,4aSR,8aRS)-6-methyl-7-(phenethoxymethylene) decahydro-1,4-methanonaphthalene, (2-(((2RS,5SR)-2-isopropyl-5-methylcyclohexylidene)methoxy)ethyl)benzene, (2-((2-(2-((R)-4-methylcyclohex-3-en-1-yl)propyl)cyclopentylidene)methoxy)ethyl)benzene, (2-((2-pentylcyclopentylidene)methoxy)ethyl)benzene, (2-((2-heptylcyclopentylidene)methoxy)ethyl)benzene, (2-((2-ethyl-4,4-dimethylcyclohexylidene)methoxy)ethyl)benzene, (2-((2-ethyl-4-methylhex-1-en-1-yl)oxy)ethyl)benzene.
Pariculary, the compound of formula (I) is selected from the group consisting of (2-((2-methylundec-1-en-1-yl)oxy) ethyl)benzene and 1-methoxy-4-(3-methyl-4-phenethoxybut-3-en-1-yl)benzene.

In a particular embodiment, at least two of the compounds of formula (II), (III) and (IV) are active compounds.

In a more particular embodiment, the compounds of formula (II), (III) and (IV) are active compounds.

According to any embodiments, the ketone of formula (II), the formate ester of formula (III) and the alcohol of formula (IV) are released from the precursor compound of formula (I) via oxidation of the precursor compound of formula (I) under ambient conditions. Even more, the precursor compound of formula (I) is oxidized under ambient conditions and in absence of any catalyst. For the sake of clarity, by the expression "ambient conditions", or the similar, it is meant the normal meaning understood by a person skilled in the art, i.e. the oxidation occurs at room temperature, under air, and atmospheric pressure. In other words, the environment wherein the compound is oxidized is air. Herewith it is understood, that the compound of formula (I) is oxidized in ambient air. In particular, it is understood that the compound of formula (I) does not require a pure oxygen environment, heat or catalyst to be oxidized.

Without intending to be limited to any particular theory, the rate at which the precursor compound of formula (I) is oxidized may be greater than, equal to, or slower than the evaporation rates of the individual ketone of formula (II), the formate esters of formula (III) or the alcohols of formula (IV).

In some embodiments, the rate at which the precursor compound of formula (I) is oxidized, and thereby, the rate at which the individual ketone of formula (II), the formate esters of formula (III) or the alcohols of formula (IV) are released intensifies or prolongs the diffusion effect, and/or perception of the characteristic fragrance of at least one active ketone formula (II), of at least one active formate ester of formula (III) and/or of at least one active alcohol of formula (IV) as defined above.

In one embodiment, 100% of the compound of formula (I) is oxidized in ambient air in a period of time ranging from 24 to 48 hours. Alternatively, 90% of the compound of formula (I) is oxidized in ambient air in a period of time ranging from 24 to 48 hours. Alternatively, 80% of the compound of formula (I) is oxidized in ambient air in a period of time ranging from 24 to 48 hours. Alternatively, 70% of the compound of formula (I) is oxidized in ambient air in a period of time ranging from 24 to 48 hours. Alternatively, 60% of the compound of formula (I) is oxidized in ambient air in a period of time ranging from 24 to 48 hours. Alternatively, 50% of the compound of formula (I) is oxidized in ambient air in a period of time ranging from 24 to 48 hours. Alternatively, 40% of the compound of formula (I) is oxidized in ambient air in a period of time ranging from 24 to 48 hours. Alternatively, 30% of the compound of formula (I) is oxidized in ambient air in a period of time ranging from 24 to 48 hours. Alternatively, 20% of the compound of formula (I) is oxidized in ambient air in a period of time ranging from 24 to 48 hours. Alternatively, 10% of the compound of formula (I) is oxidized in ambient air in a period of time ranging from 24 to 48 hours. Alternatively, 9% of the compound of formula (I) is oxidized in ambient air in a period of time ranging from 24 to 48 hours. Alternatively, 8% of the compound of formula (I) is oxidized in ambient air in a period of time ranging from 24 to 48 hours. Alternatively, 7% of the compound of formula (I) is oxidized in ambient air in a period of time ranging from 24 to 48 hours. Alternatively, 6% of the compound of formula (I) is oxidized in ambient air in a period of time ranging from 24 to 48 hours. Alternatively, 5% of the compound of formula (I) is oxidized in ambient air in a period of time ranging from 24 to 48 hours. Alternatively, 4% of the compound of formula (I) is oxidized in ambient air in a period of time ranging from 24 to 48 hours. Alternatively, 3% of the compound of formula (I) is oxidized in ambient air in a period of time ranging from 24 to 48 hours. Alternatively, 2% of the compound of formula (I) is oxidized in ambient air in a period of time ranging from 24 to 48 hours. Alternatively, 1% of the compound of formula (I) is oxidized in ambient air in a period of time ranging from 24 to 48 hours.

In a particular embodiment, the compound of formula (I) is encapsulated. At least one compound of formula (I) can be encapsulated in a microcapsule. In a preferred embodiment, at least one compound of formula (I) is encapsulated in a core-shell microcapsule wherein the compound of formula (I) is contained in the core surrounded by the shell. The shell of the microcapsule protects the compound of formula (I) from the environment. The shell is made of material which is able to release the compound of formula (I) and/or the active compound of formulas (II), (III) and/or (IV). In a preferred embodiment, the shell is made of material which is able to release the compound of formula (I) and/or the active compound of formulas (II), (III) and/or (IV) upon breakage of the shell and/or by diffusion through the shell. A person skilled in the art is well aware of processes to prepare said microcapsules.

The nature of the polymeric shell from the microcapsules of the invention can vary. As non-limiting examples, the shell can be aminoplast-based, polyurea-based or polyurethane-based. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to another embodiment the shell is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer).

According to another embodiment, the emulsifier is an anionic or amphiphilic biopolymer preferably chosen from the group consisting of gum Arabic, soy protein, gelatin, sodium caseinate and mixtures thereof.

According to another embodiment, the shell is polyurethane-based made from, for example but not limited to polyisocyanate and polyols, polyamide, polyester, etc.

The preparation of an aqueous dispersion/slurry of core-shell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together
    a) a polyamine component in the form of melamine or of a mixture of melamine and at least one $C_1$-$C_4$ compound comprising two $NH_2$ functional groups;
    b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
    c) a protic acid catalyst;
2) preparing an oil-in-water dispersion, wherein the droplet size is comprised between 1 and 600 μm, and comprising:
    i. an oil;
    ii. a water medium
    iii. at least an oligomeric composition as obtained in step 1;
    iv. at least a cross-linker selected amongst
    A) $C_4$-$C_{12}$ aromatic or aliphatic di- or tri-isocyanates and their biurets, triurets, trimmers, trimethylol propane-adduct and mixtures thereof; and/or
    B) a di- or tri-oxiran compounds of formula A-(oxiran-2-ylmethyl)$_n$
      wherein n stands for 2 or 3 and 1 represents a $C_2$-$C_6$ group optionally comprising from 2 to 6 nitrogen and/or oxygen atoms;
    v. optionally a $C_1$-$C_4$ compounds comprising two $NH_2$ functional groups;
3) Heating said dispersion;
4) Cooling said dispersion.
This process is described in more details in WO 2013/068255, the content of which is included by reference.

According to another embodiment, the shell of the microcapsule is polyurea- or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 µm, preferably between 5 and 50 µm;
d) Applying conditions sufficient to induce interfacial polymerisation and form microcapsules in form of a slurry.

In a particular embodiment, encapsulation of a compound of formula (I) may provide an environment within the capsule wherein all, or a portion of the compound of formula (I) may oxidize, thereby releasing the individual ketone of formula (II), the formate esters of formula (III) or the alcohols of formula (IV) into the capsule. In a preferred embodiment, the shell of the microcapsule may act as a permeability barrier, preventing the leakage of the individual ketone of formula (II), the formate esters of formula (III) or the alcohols of formula (IV) from the capsule.

In a second aspect, the present invention relates to a method or a process to confer, enhance, improve or modify the odor properties of a perfuming composition, the air surrounding the perfuming composition, a surface or a perfumed article, comprising adding to the composition, the air, or article, or contacting or treating the surface with an effective amount of at least one compound of formula (I) as defined above. The term "surface", as used herein may refer to a user's skin, hair, a textile, or hard surface, on to which, a perfume composition comprising or containing at least one compound of formula (I) is applied.

In a third aspect, the present invention relates to a method for intensifying or prolonging the diffusion effect of the characteristic fragrance of at least one active ketone formula (II), of at least one active formate ester of formula (III) and/or of at least one active alcohol of formula (IV) as defined above, on a surface or the air surrounding the perfuming composition, wherein the surface, or the air is treated with at least one compound (I) as defined above, or with a composition or article containing at least one compound (I), under conditions susceptible of allowing the release of at least one active ketone formula (II), of at least one active formate ester of formula (III) and/or of at least one active alcohol of formula (IV) over time.

In a fourth aspect, the present invention relates to a perfuming composition comprising i) at least one compound of formula (I), as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cy Mel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bone et al. Chimia, 2011, vol. 65, pages 177-181.

The term "perfumery base" is understood as a composition comprising at least one perfuming co-ingredient.

The perfuming co-ingredient is not a compound according to the invention. Moreover, the term "perfuming co-ingredient" is understood as a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpene hydrocarbons, nitrogenous or *sulphurous* heterocyclic compounds and essential oils, and the perfuming co-ingredients can be of natural or synthetic origin.

In particular one may cite perfuming co-ingredients knows for having a similar olfactive note, such as:

In particular, one may cite perfuming co-ingredients which are commonly used in perfume formulations, such as:
Aldehydic ingredients: decanal, dodecanal, 2-methyl-undecanal, 10-undecenal, octanal and/or nonenal;
Aromatic-herbal ingredients: eucalyptus oil, camphor, eucalyptol, menthol and/or alpha-pinene;
Balsamic ingredients: coumarine, ethylvanillin and/or vanillin;
Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
Floral ingredients:Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl(S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methylionones isomers;
Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
Green ingredients: 2,4-dimethyl-3-cyclohexene-1-carbaldehyde, 2-tert-butyl-1-cyclohexyl acetate, styrallyl acetate, allyl(2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;
Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethylcyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;
Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol,
Methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;
Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

The term "perfumery adjuvant" is understood as an ingredient capable of imparting additional added benefit such as a color, a particular light resistance, chemical stability and etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one of the invention's compounds of formula (I) and at least one perfumery carrier represents a particular embodiment of the invention as well as a perfuming composition comprising at least one of the invention's compounds, at least one perfumery carrier, at least one perfumery base, and optionally at least one perfumery adjuvant.

It is useful to mention here that the possibility to have, in the compositions mentioned above, more than one of the invention's compounds or other precursors of similar type is important as it enables the perfumer to prepare accords, perfumes, possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as the mixture does not provide the inventive compound in a suitable form for perfumery. Thus, unpurified reaction mixtures are generally excluded from the present invention unless otherwise specified.

Furthermore, the invention's compounds can also be advantageously used in all the fields of modern perfumery, i.e. fine or functional perfumery, to positively impart or modify the odor of a consumer product into which the compound (I) is added.

In a fifth aspect, thus, the present invention relates to a perfumed consumer product comprising at least one compound of formula (I), as defined above or a perfuming composition as defined above.

For the sake of clarity, it has to be mentioned that, the term "perfumed consumer product" is understood as a consumer product which is expected to deliver at least a pleasant perfuming effect to the surface to which it is applied (e.g. skin, hair, textile, or hard surface). In other words, a perfumed consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

In a particular embodiment, the perfumed consumer product is a perfume, a fabric care product, a body-care product, a cosmetic preparation, a skin-care product, an air care product or a home care product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, Vol. 20, Wiley-VCH, Weinheim, p. 355-540 (2012); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the compounds of the invention based on the weight of the composition into which they are incorporated. Concentrations lower than these, such as in the order of 0.001% to 5% by weight, can be used when these compounds are applied directly in the perfuming or flavoring of the various consumer products mentioned hereinabove.

In a sixth aspect, the present invention relates to a compound of formula

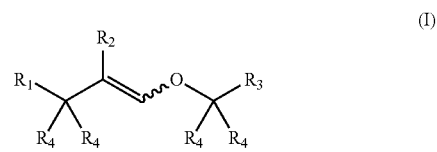

wherein $R_1$ represents a $C_{1-15}$ alkyl, $C_{2-15}$ alkenyl, $C_{3-15}$ cycloalkyl, $C_{5-15}$ cycloalkenyl or $C_{6-10}$ aryl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

$R_2$ represents a $C_{1-15}$ alkyl group;

$R_1$ and $R_2$, when taken together, form a $C_{5-15}$ cycloalkyl, $C_{5-15}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid, 4-methylcyclohex-3-en-1-yl and/or $C_{1-4}$ carboxylic ester group, wherein the heteroatom represents one or more of an oxygen atom;

$R_3$ represents a $C_{1-15}$ alkyl, $C_{3-15}$ alkenyl, $C_{3-15}$ cycloalkyl or $C_{5-15}$ cycloalkenyl group, each optionally substituted with one or more a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

$R_4$, each independently, represent a hydrogen or a $C_{1-5}$ alkyl group;

$R_1$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

$R_3$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and Compound of formula (I) is a $C_{1-6}$-$C_{28}$ compounds provided that when $R_1$ is methyl group then $R_2$ is not methyl or ethyl group, when $R_1$ is ethyl group then $R_2$ is not ethyl group, when $R_3$ is an unsubstituted methyl group then $R_4$ is not hydrogen atom or methyl group, when $R_3$ is an unsubstituted ethyl group then $R_4$ is not hydrogen atom, provided that the following compounds are excluded:

(((3,7-dimethylocta-1,6-dien-3-yl)oxy)methylene)cyclohexane, 3-(((2-ethylhex-1-en-1-yl)oxy)methyl)heptane, 4-(((7-methyloctyl)oxy)methylene)cyclohex-1-ene, 4-((dodecyloxy)methylene)cyclohex-1-ene, (4-((4-phenylbutoxy)methylene)cyclohexyl)benzene, 1-((2-ethylhex-1-en-1-yl)oxy)octane, 1-((2-ethylhex-1-en-1-yl)oxy)dodecane, 2-ethylhexenyl lauryl ether, 2-ethylhexenyl octyl ether, 1-(2'-ethylhexoxy)-2-ethyl-1,3-hexadiene, 1-((2-methylpent-1-en-1-yl)oxy)dodecane, 3-(cyclohexylidenemethoxy)-1,5,5-trimethylcyclohex-1-ene, (3-(benzyloxy)-2-methylallyl)benzene and 4-(4-(allyloxy)-3-methylbut-3-en-1-yl)-1,2-dimethoxybenzene.

Exemplary embodiments of compounds of formula (I) are as described above.

In a preferred embodiment, the following moiety of formula (I)

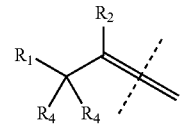

corresponds to the ketone of formula (II) as defined above.

In a preferred embodiment, the following moiety of formula (I)

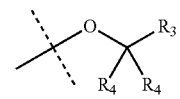

corresponds to the alcohol of formula (IV) as defined above.

In a further aspect, the present invention also relates to a microcapsule comprising at least one compound of formula (I). In a preferred embodiment, the at least one compound of formula (I) is encapsulated in a core-shell microcapsule wherein the at least one compound of formula (I) is contained in the core surrounded by the shell. In a preferred embodiment, the shell of the microcapsule protects the compound of formula (I) from the environment. The shell is made of material which is able to release the at least one compound of formula (I) and/or the compound of formulas (II), (III) and/or (IV). In a preferred embodiment, the shell is made of material which is able to release the compound of formula (I) and/or the compound of formulas (II), (III) and/or (IV) upon breakage of the shell and/or by diffusion through the shell. A person skilled in the art is well aware of processes to prepare said microcapsules.

In a further aspect, the present invention also relates to the use of precursor compounds for releasing compounds selected from the group consisting of a) a ketone of formula

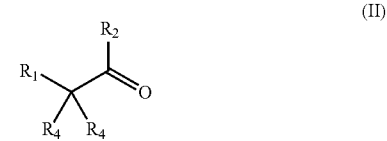

(II)

wherein $R_4$ represents a $C_{1-15}$ alkyl, $C_{2-15}$ alkenyl, $C_{3-15}$ cycloalkyl, $C_{5-15}$ cycloalkenyl group or $C_{6-10}$ aryl, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl group, $C_{1-8}$ alkoxy, hydroxy, carboxylic acid group and/or $C_{1-4}$ carboxylic ester group;

$R_2$ represents a $C_{1-15}$ alkyl group;

$R_1$ and $R_2$, when taken together, form a $C_{5-15}$ cycloalkyl, $C_{5-15}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid, 4-methylcyclohex-3-en-1-yl and/or $C_{1-4}$ carboxylic ester group, wherein the heteroatom represents one or more of an oxygen;

$R_4$, each independently, represent a hydrogen or a $C_{1-5}$ alkyl group; and $R_1$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

b) a formate ester of formula

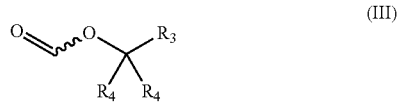

(III)

wherein $R_3$ represents a $C_{1-15}$ alkyl, $C_{2-15}$ alkenyl, $C_{3-15}$ cycloalkyl or $C_{5-15}$ cycloalkenyl group, each optionally substituted with one or more a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and $R_4$ has the same meaning as defined above; and $R_3$ and $R_4$, when taken together, form a $C_{3-15}$ cycloalkyl or $C_{5-15}$ cycloalkeny group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

c) an alcohol of formula

(IV)

wherein $R_3$ and $R_4$ have the same meaning as defined above;

wherein at least one of the compounds of formula (II), (III) or (IV) is an active compound;

wherein the precursor compound comprises a compound of formula (I)

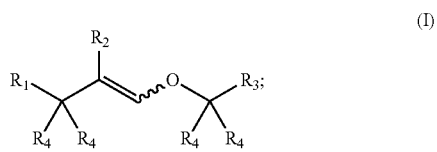

(I)

wherein $R_1$; $R_2$, $R_3$ and $R_4$ have the same meaning as defined above, by exposing the precursor compound to an environment wherein the compound is oxidized.

In a further aspect, the present invention relates to the use of at least one compound of formula (I) as defined above to confer, enhance, improve or modify the odor properties of a perfuming composition, the air surrounding the perfuming composition, a surface, or of a perfumed article, comprising adding to the composition or article or contacting or treating the surface with an effective amount of at least one compound of formula (I) as defined above. The term "surface", as used herein may refer to a user's skin, hair, a textile, or hard surface, on to which, a perfume composition comprising or containing the at least one compound of formula (I) is applied.

In a further aspect, the present invention relates to the use of at least one compound of formula (I) as defined above for intensifying or prolonging the diffusion effect, and/or perception of the characteristic fragrance of at least one active ketone formula (II), of at least one formate ester of formula (III) and/or of at least one alcohol of formula (IV) as defined above, on a surface, wherein the surface is treated with at least one compound of formula (I) as defined above, or with a composition or article containing the at least one compound of formula (I), under conditions susceptible of allowing the release of the at least one ketone formula (II), of at least one formate ester of formula (III) and/or of at least one active alcohol of formula (IV) over time.

EXAMPLES

1. Preparation of the Compounds

The following compounds have been prepared and characterized. Mass spectral data (EI, 70 eV), major fragments ions and relative abundance, and NMR data are provided for only the E-isomer (generally the major isomer), unless otherwise noted. NMR spectra were recorded using $CDCl_3$ as solvent. The chemical displacements δ are indicated in ppm with respect to TMS as standard, the coupling constants J are expressed in Hz.

Examples 1-6

The dimethyl acetal (35 mmol), alcohol (70 mmol), and $KHSO_4$ (48 mg, 0.35 mmol) were added to a 25 ml, round-bottomed flask equipped with a distillation head and nitrogen bubbler. The mixture was heated (oil bath at 150° C.) while distilling out the liberated methanol (vapor temperature 64° C.) until the vapor temperature dropped (40-60 min) signaling that most of the methanol had been removed. The mixture was placed under vacuum (300 mTorr) and heated (180-190° C. oil bath) for 2-3 h while allowing liberated alcohol to distill from the reaction flask. The enol ethers were isolated by vacuum distillation from the reaction flask after adding $Na_2CO_3$ (0.5 g) or by silica gel flash chromatography followed by Kugelrohr distillation.

Example 1. (2-((2-methylundec-1-en-1-yl)oxy) ethyl)benzene

Starting from the dimethyl acetal of 2-methylundecanal and 2-phenylethanol, the title compound was isolated by distillation (bp 130° C., 30 mTorr) as a colorless oil in 91% yield (E/Z=59:41).

$^1$H NMR ($CDCl_3$, 500 MHz, E-isomer): δ 0.88 (t, J=7.0 Hz, 3H), 1.19-1.39 (m, 14H), 1.57 (s, 3H), 1.85 (t, J=7.5 Hz, 2H), 2.91 (t, J=7.3 Hz, 2H), 3.86 (t, J=7.3 Hz, 2H), 5.81 (s, 1H), 7.17-7.30 (m, 5H).

Example 2. (2-((2-methylundec-1-en-1-yl)oxy) ethoxy)benzene

Starting from the dimethyl acetal of 2-methylundecanal and 2-phenoxyethanol, the title compound was isolated by distillation (bp 128-130° C., 25 mTorr) as a colorless oil in 90% yield (E/Z=60:40).

$^1$H NMR (CDCl$_3$, 600 MHz, E-isomer): δ 0.88 (t, J=7.0 Hz, 3H), 1.19-1.39 (m, 14H), 1.58 (s, 3H), 1.85 (t, J=7.4 Hz, 2H), 4.00 (t, J=5.0 Hz, 2H), 4.12 (t, J=5.0 Hz, 2H), 5.89 (s, 1H), 6.89-6.96 (m, 3H), 7.24-7.30 (m, 2H).

Example 3. (3-methyl-4-phenethoxybut-3-en-1-yl)benzene

Starting from the dimethyl acetal of 2-methyl-4-phenylbutanal and 2-phenylethanol, the title compound was isolated by distillation (bp 135° C., 30 mTorr) as a colorless oil in 83% yield (E/Z=52:48).

$^1$H NMR (CDCl$_3$, 600 MHz, E-isomer): δ 1.64 (d, J=1.2 Hz, 3H), 2.16 (t, J=7.9 Hz 2H), 2.66 (t, J=7.9 Hz, 2H), 2.83 (t, J=7.2 Hz, 2H), 3.81 (t, J=7.2 Hz, 2H), 5.76 (q, J=1.2 Hz, 1H), 7.11-7.30 (m, 10H).

Example 4. 1-methoxy-4-(2-methyl-3-phenethoxyallyl)benzene

Starting from the dimethyl acetal of 3-(4-methoxyphenyl)-2-methylpropanal and 2-phenylethanol, the title compound was isolated by distillation (bp 155-158° C., 30 mTorr) as a colorless oil in 77% yield (E/Z=56:44).

$^1$H NMR (CDCl$_3$, 600 MHz, E-isomer): δ 1.5 (s, 3H), 2.92 (t, J=7.2 Hz, 2H), 3.09 (s, 2H), 3.76 (s, 3H), 3.90 (t, J=7.2 Hz, 2H), 5.91 (s, 1H), 6.79-6.82 (m, 2H), 7.03-7.08 (m, 2H), 7.18-7.31 (m, 5H).

Example 5. (2-((2-methyl-4-(2,6,6-trimethylcyclohex-1-en-1-yl)but-1-en-1-yl)oxy)ethyl)benzene Starting from the dimethyl acetal of 2-methyl-4-(2,6,6-trimethylcyclohex-1-en-1-yl)butanal and 2-phenylethanol, the title compound was isolated by silica gel flash chromatorgraphy (hexane/EtOAc, 98:3) followed by Kugelrohr distillation (180° C., 30 mTorr) as a colorless oil in 74% yield (E/Z=45:55).

$^1$H NMR (CDCl$_3$, 600 MHz, E-isomer): δ 0.98 (s, 3H), 1.00 (s, 3H), 1.39-1.44 (m, 2H), 1.54-1.59 (m, 2H), 1.60 (s, 3H), 1.64 (s, 3H), 1.86-194 (m, 3H), 1.99-2.06 (m, 2H), 2.07-2.13 (m, 1H), 2.93 (t, J=7.1 Hz, 2H), 3.88 (t, J=7.1 Hz, 2H), 5.86 (s, 1H), 7.18-7.24 (m, 3H), 7.25-7.31 (m, 2H).

Example 6. (2-((2,2,6-trimethylcyclohexylidene) methoxy)ethyl)benzene

Starting from the dimethyl acetal of 2,2,6-trimethylcyclohexane-1-carbaldehyde and 2-phenylethanol, the title compound was isolated by silica gel flash chromatorgraphy (hexane/EtOAc, 98:2) followed by Kugelrohr distillation (130-150° C., 40 mTorr) as a pale amber oil in 70% yield (E/Z=76:24). $^1$H NMR (CDCl$_3$, 500 MHz, E-isomer): δ 1.00 (s, 3H), 1.07 (s, 3H), 1.11 (d, J=7.4 Hz, 3H), 1.19-1.77 (m, 6H), 2.90 (t, J=7.0 Hz, 2H), 2.91-3.05 (m, 1H), 3.87 (t, J=7.0 Hz, 2H), 5.83 (s, 1H), 7.17-7.31 (m, 5H).

Examples 7-8

A toluene solution (100 ml) of the aldehyde (30-25 mmol), 1-octanol (2.5 equiv) and TsOH (0.02 equiv) was heated at reflux for 2-3 h. The water of reaction was removed with a Dean-Stark trap. The reaction mixture was diluted with EtOAc and then washed with sat. NaHCO$_3$ and water. The organic phase was dried with Na$_2$SO$_4$, filtered and concentrated to afford the crude dioctyl acetal. This material was mixed with KHSO$_4$ (0.02 equiv) and heated for 1-2 h at 180° C. under vacuum (35 Torr) using a Kugelrohr distillation apparatus. The remaining residue then was subjected to Kugelrohr distillation to obtain the enol ether (typical conditions, 140-170° C., 50 mTorr).

Example 7. 2-methyl-1-(octyloxy)undec-1-ene

Starting from 2-methylundecanal, the title compound was isolated as a colorless liquid in 53% yield (E/Z=50:50).

$^1$H NMR (CDCl$_3$, 500 MHz, E-isomer): δ 0.88 (t, J=6.9 Hz, 6H), 1.20-1.40 (m, 24H), 1.54-1.64 (m, 2H), 1.58 (s, 3H), 1.85 (t, J=7.4 Hz, 2H), 3.65 (t, J=6.7 Hz, 2H), 5.80 (s, 1H).

Example 8. (3-methyl-4-(octyloxy)but-3-en-1-yl) benzene

Starting from 2-methyl-4-phenylbutanal, the title compound was isolated as a colorless liquid in 57% yield (E/Z=58:42).

$^1$H NMR (CDCl$_3$, 600 MHz, E-isomer): δ 0.88 (t, J=6.9 Hz, 3H), 1.21-1.38 (m, 10H), 1.51-1.58 (m, 2H), 1.66 (s, 3H), 2.16 (t, J=8.0 Hz, 2H), 2.67 (t, J=8.0 Hz, 2H), 3.61 (t, J=6.7 Hz, 2H), 5.77 (s, 1H), 7.13-7.28 (m, 5H).

Example 9. 1-methoxy-4-(3-methyl-4-phenethoxybut-3-en-1-yl)benzene

Methoxymethyltriphenylphosphonium chloride (17.7 g, 51.7 mmol) and 4-(4-methoxyphenyl)butan-2-one (6.12 g, 34.3 mmol) were added to 150 ml of toluene. Potassium f-butoxide (6.18 g, 55.1 mmol) was added to the stirring slurry in 4 portions every 15 min. The mixture was stirred for another 4 h during which time it became a pale yellow, homogeneous solution. It then was poured into 200 ml of water and extracted with diethyl ether (3×100 mL). The organic phases were combined, dried over MgSO$_4$, filtered and concentrated. The residue was subjected to silica gel flash chromatography (hexane/CH$_2$Cl$_2$ 100:0→75:25) affording 4.06 g (19.7 mmol) of the methyl enol ether product. This material (3.8 g, 18.4 mmol) was combined with 2-phenylethanol (4.5 g, 36.8 mmol) and KHSO$_4$ (0.027 g, 0.198 mmol) in a round-bottomed flask (25 mL) equipped with a distillation head and nitrogen bubbler. The mixture was heated for 1 h at 150° C. and liberated methanol was distilled from the mixture. The mixture then was placed under vacuum (300 mTorr) and heated at 1900 for 2 h while allowing the excess 2-phenylethanol to distill from the flask. Na$_2$CO$_3$ (0.3 g) was added to the flask and the title compound (4.46 g, 15.1 mmol) was isolated by distillation (bp 170° C., 30 mTorr) as a colorless oil (E/Z=57:43) in 82% yield.

$^1$H NMR (CDCl$_3$, 600 MHz, E-isomer): δ 1.63 (d, J=1.2 Hz, 3H), 2.13 (br t, J=7.9 Hz, 2H), 2.61 (m, 2H), 2.86 (t, J=7.2 Hz, 2H), 3.76 (s, 3H), 3.84 (t, J=7.2 Hz, 2H), 5.77 (q, J=1.2 Hz, 1H), 6.80 (d, J=8.6 Hz, 2H), 7.07 (d, J=8.6 Hz, 2H), 7.17-7.31 (m, 5H).

Examples 10-14

A toluene solution (100 ml) of the aldehyde (30-25 mmol), 3-octanol (2.5 equiv) and TsOH (0.02 equiv) was heated at reflux for 3-4 h. The water of reaction was removed with a Dean-Stark trap. The reaction mixture was diluted with EtOAc and then washed with sat. NaHCO$_3$ and water. The organic phase was dried with Na$_2$SO$_4$, filtered and concentrated. The residue was subjected to Kugelrohr distillation to first remove the excess 3-octanol (typical conditions, 90° C., 50 mTorr) and then to obtain the enol ether (typical conditions, 140-170° C., 50 mTorr).

Example 10.
2-methyl-1-(octan-3-yloxy)undec-1-ene

Starting from 2-methylundecanal, the title compound was isolated as a colorless oil in 46% yield (E/Z=61:39).
$^1$H NMR (CDCl$_3$, 500 MHz, E-isomer): δ 0.88 (t, J=7.1 Hz, 3H), 0.89 (t, J=7.1 Hz, 3H), 0.90 (t, J=7.3 Hz, 3H), 1.20-1.56 (m, 24H), 1.58 (s, 3H), 1.85 (t, J=7.4 Hz, 2H), 3.42 (quint, J=5.7 Hz, 1H), 5.81 (s, 1H).

Example 11. (3-methyl-4-(octan-3-yloxy)but-3-en-1-yl)benzene

Starting from 2-methyl-4-phenylbutanal, the title compound was isolated as a colorless oil in 56% yield (E/Z=58:42).
$^1$H NMR (CDCl$_3$, 600 MHz, E-isomer): δ 0.86 (t, J=7.4 Hz, 3H), 0.89 (t, J=7.0 Hz, 3H), 1.21-1.53 (m, 10H), 1.65 (s, 3H), 2.16 (t, J=7.9 Hz, 2H), 2.67 (t, J=7.9 Hz, 2H), 3.37 (quintet, J=6.1 Hz, 1H), 5.76 (s, 1H), 7.12-7.29 (m, 5H).

Example 12. 1-methoxy-4-(2-methyl-3-(octan-3-yloxy)allyl)benzene

Starting from 3-(4-methoxyphenyl)-2-methylpropanal, the title compound was isolated as a colorless oil in 53% yield (E/Z=59:41).
$^1$H NMR (CDCl$_3$, 500 MHz, E-isomer): δ 0.89 (t, J=7.0 Hz, 3H), 0.92 (t, J=7.4 Hz, 3H), 1.24-1.36 (m, 5H), 1.36-1.61 (m, 5H), 1.51 (s, 3H), 3.10 (s, 2H), 3.49 (quint, J=6.3 Hz, 1H), 3.77 (s, 3H), 5.95 (s, 1H), 6.80-6.82 (m 2H), 7.06-7.09 (m, 2H).

Example 13. 1,3,3-trimethyl-2-(3-methyl-4-(octan-3-yloxy)but-3-en-1-yl)cyclohex-1-ene Starting from 2,2,6-trimethylcyclohexane-1-carbaldehyde, the title compound was isolated after two sequential Kugelrohr distillations as a colorless oil in 38% yield (E/Z=50:50).
$^1$H NMR (CDCl$_3$, 500 MHz, E-isomer): δ 0.86-0.92 (overlapping triplets, 6H), 0.99 (s, 3H), 1.02 (s, 3H), 1.22-1.60 (m, 14H), 1.60 (s, 3H), 1.65 (s, 3H), 1.87-1.94 (m, 3H), 2.00-2.13 (m, 3H), 3.44 (quint, J=6.0 Hz, 1H), 5.86 (s, 1H).

Example 14.
((2-methylundec-1-en-1-yl)oxy)cyclododecane

A mixture of 2-methylundecanal (4.17 g, 22.6 mmol), cyclododecanol (4.24 g, 23 mmol), TsOH (0.08 g, 0.421 mmol) and toluene (50 mL) was heated at reflux for 2 h while removing the water of reaction with a Dean-Stark trap. After the mixture cooled, it was diluted with EtOAc and washed with sat. NaHCO$_3$ and sat. NaCl. The organic phase was dried with Na$_2$SO$_4$, filtered and concentrated. The residue was subjected to Kugelrohr distillation (160-180° C., 50 mTorr) affording 2.54 g of the title compound (7.24 mmol, 32% yield) as a colorless oil (E/Z=55:45).

$^1$H NMR (CDCl$_3$, 500 MHz, E-isomer): δ 0.88 (t, J=6.9 Hz, 3H), 1.20-1.45 (m, 32H), 1.46-1.59 (m, 2H), 1.57 (s, 3H), 1.59-1.70 (m, 2H), 1.85 (t, J=7.4 Hz, 2H), 3.67 (quint, J=7.5 Hz, 1H) 5.82 (s, 1H).

Example 15. 1-((2,6-dimethyloct-7-en-2-yl)oxy)-2-methylundec-1-ene

A hexane solution (100 ml) of 2-methylundecanal (14.9 g, 81 mmol), dihydromyrcenol (25.4 g, 163 mmol) and TsOH (0.31 g, 1.63 mmol) was heated at reflux for 5 h while removing the water of reaction with a Dean-Stark trap. The mixture was diluted with additional hexane and washed with sat. Na$_2$CO$_3$ and brine. The organic phase was dried with Na$_2$SO$_4$, filtered and concentrated. After adding Na$_2$CO$_3$ (1 g), the residue was subjected to short-path distillation (bp 138° C., 30 mTorr) affording 2.2 g of the title compound (6.82 mmol, 8% yield) (E/Z=61:39) as a colorless oil (E/Z=61:39).
$^1$H NMR (CDCl$_3$, 600 MHz, E-isomer): δ 0.88 (t, J=7.0 Hz, 3H), 0.98 (d, J=6.9 Hz, 3H), 1.19 (s, 6H), 1.21-1.39 (m, 18H), 1.40-1.50 (m, 2H), 1.57 (s, 3H), 1.87 (t, J=7.4 Hz, 2H), 2.12 (septet, J=6.9 Hz, 2H), 4.90 (d, J=10.3 Hz, 1H), 4.95 (d, J=17.1 Hz, 1H), 5.69 (m, 1H), 5.96 (s, 1H).

Example 16. 1-(((Z)-hex-3-en-1-yl)oxy)-2-methyl-undec-1-ene

The dimethyl acetal of 2-methylundecanal (20 g, 87 mmol), cis-3-hexen-1-ol (26.1 g, 260 mmol), and KHSO$_4$ (0.118 g, 0.87 mmol) were added to a 100 ml, round-bottomed flask equipped with a Vigreux column (12 cm), distillation head and nitrogen bubbler. The mixture was heated at 150° C. for 1 h while distilling out liberated methanol. The Vigreux column was removed and heating was continued at 190° C. for 1 h while allowing liberated cis-3-hexen-1-ol to distill from the reaction flask. The mixture was allowed to cool, placed under vacuum (5 Torr) and heated at 130° C. for 3 h to remove remaining hexenol. The enol ether then was isolated by vacuum distillation from the reaction flask (bp 120-130° C., 25 mTorr) followed by a Kugelrohr distillation (1150, 25 mTorr) to afford the title compound (17.0 g, 63.8 mmol) as a colorless liquid in 73% yield (E/Z=56:44).
$^1$H NMR (CDCl$_3$, 600 MHz, E-isomer): δ 0.88 (t, J=7.0 Hz, 3H), 0.96 (t, J=7.5 Hz, 3H), 1.20-1.40 (m, 14H), 1.58 (s, 3H), 1.85 (t, J=7.5 Hz, 2H), 2.03-2.09 (m, 2H), 2.31-2.38 (m, 2H), 3.65 (t, J=7.0 Hz, 2H), 5.30-5.37 (m, 1H), 5.44-5.51 (m, 1H), 5.81 (s, 1H).

Examples 17-19

The dimethyl acetal (35-60 mmol), alcohol (2 equiv mmol), and KHSO$_4$ (48 mg, 0.35 mmol) were added to a 25-50 ml, round-bottomed flask equipped with a distillation head and nitrogen bubbler. The mixture was heated (oil bath at 150° C.) while distilling out the liberated methanol (vapor temperature 64° C.) until the vapor temperature dropped (40-60 min) signaling that most of the methanol had been removed. The mixture was placed under vacuum (300-500 mTorr) and heated (180-190° C. oil bath) for 2-3 h while allowing liberated alcohol to distill from the reaction flask. The enol ethers were isolated by vacuum distillation from the reaction flask after adding Na$_2$CO$_3$ (0.25-0.5 g) or by silica gel flash chromatography followed by Kugelrohr distillation.

Example 17. (2-((2-methyldec-1-en-1-yl)oxy)ethyl) benzene

Starting from the dimethyl acetal of 2-methyldecanal and 2-phenylethanol, the title compound was isolated by distillation (bp 140-145° C., 20 mTorr) as a slightly yellow oil in 86% yield (E/Z=60:40).

$^1$H NMR (CDCl$_3$, 500 MHz, E-isomer): δ 0.88 (t, J=6.9 Hz, 3H), 1.19-1.39 (m, 12H), 1.57 (s, 3H), 1.85 (t, J=7.4 Hz, 2H), 2.92 (t, J=7.3 Hz, 2H), 3.87 (t, J=7.3 Hz, 2H), 5.82 (s, 1H), 7.17-7.30 (m, 5H).

Example 18. 1-((3,7-dimethyloct-6-en-1-yl)oxy)-2-methylundec-1-ene

Starting from the dimethyl acetal of 2-methylundecanal and citronellol, the title compound was isolated by distillation (bp 160° C., 50 mTorr) as a pale yellow oil in 83% yield (E/Z=58:42).

$^1$H NMR (CDCl$_3$, 500 MHz, E-isomer): δ 0.88 (t, J=7.1 Hz, 3H), 0.90 (d, J=6.7 Hz, 3H), 1.22-1.45 (m, 17H), 1.56 (s, 3H), 1.60 (s, 3H), 1.68 (s, 3H), 1.55-1.73 (m, 2H), 1.85 (t, J=7.5 Hz, 2H), 1.90-2.03 (m, 2H), 3.62-3.73 (m, 2H), 5.09 (t, J=7.3 Hz, 2H), 5.80 (s, 1H).

Example 19. (2-((2-ethylhex-1-en-1-yl)oxy)ethyl) benzene

Starting from the dimethyl acetal of 2-ethylhexanal and 2-phenylethanol, the title compound was isolated by distillation (bp 140-145° C., 500 mTorr) as a pale yellow oil in 77% yield (isomer ratio=57:43).

$^1$H NMR (CDCl$_3$, 500 MHz, isomer mixture): δ 0.89 (t, J=7.0 Hz, 3H), 0.94, 0.96 (triplets, J=7.6 Hz, 3H), 1.23-1.36 (m, 4H), 1.88, 1.89 (quartets, J=7.6 Hz, 2H), 2.05, 2.07 (triplets, J=7.4 Hz, 2H), 2.90 (t, J=7.1 Hz, 2H), 3.84, 3.85 (triplets, J=7.1 Hz, 2H), 5.77, 5.80$_{major\ isomer}$ (singlets, 1H), 7.17-7.31 (m, 5H).

Examples 20-29

Methoxymethyltriphenylphosphonium chloride (15.1 g, 44.1 mmol) and the ketone (29.4 mmol) were added to 120 ml of toluene. Potassium f-butoxide (5.27 g, 47 mmol) was added to the stirring slurry in 4 portions every 15 min. The mixture was stirred for 4 h becoming a deep red color. It then was poured into 500 ml of water and extracted with EtOAc (3×250 mL). The organic phases were combined, dried over Na$_2$SO$_4$, filtered and concentrated. The resulting methyl enol ether product was isolated by flash chromatography (silica gel, hexane) followed by Kugelrohr distillation. The methyl enol ether (30-60 mmol) then was combined with 2-phenylethanol (2 equiv) and KHSO$_4$ (1 mole %) in a round-bottomed flask (50 mL) equipped with a distillation head and nitrogen bubbler. The mixture was heated (oil bath at 150° C.) while distilling out the liberated methanol (vapor temperature 64° C.) until the vapor temperature dropped (typically 40 min). The mixture then was placed under vacuum (300 mTorr) and heated at 180° C. while allowing the excess 2-phenylethanol to distill from the flask (typically 2 h). The resulting enol ethers were isolated by vacuum distillation from the reaction flask after adding Na$_2$CO$_3$ (0.25 g) or by silica gel flash chromatography. Product yields are reported for the conversion of the intermediate methyl enol ethers to the isolated products.

Example 20. (phenethoxymethylene)cyclopentadecane

The title compound was prepared starting from cyclopentadecanone. It was isolated by short-path distillation (bp>170° C., 25 mTorr) from the crude reaction mixture as a colorless oil in 45% yield from the intermediate methyl enol ether.

$^1$H NMR (CDCl$_3$, 500 MHz): δ 1.16-1.52 (m, 24H), 1.87 (t, J=7.1 Hz, 2H), 2.03 (d, J=7.4 Hz, 2H), 2.90 (t, J=7.1 Hz, 2H), 3.85 (t, J=7.1 Hz, 2H), 5.82 (s, 1H), 7.17-7.31 (m, 5H).

Example 21. (2-((4-(tert-pentyl)cyclohexylidene) methoxy)ethyl)benzene

The title compound was prepared starting from 4-(tert-pentyl)cyclohexan-1-one. It was isolated by silica gel flash chromatography (hexane/EtOAc, 100:0->95:5) as a colorless oil in 24% yield from the intermediate methyl enol ether.

$^1$H NMR (CDCl$_3$, 500 MHz): δ 0.78 (s, 6H), 0.79 (t, J=7.5 Hz, 3H), 0.96 (qt, J=12.7, 3.9 Hz, 2H), 1.20 (tt, J=12.0, 2.8 Hz, 1H), 1.25 (q, J=7.5 Hz, 2H), 1.57 (t, J=13.4 Hz, 1H), 1.75 (m, 2H), 1.85 (t, J=13.4 Hz, 1H), 2.08 (d, J=13.4 Hz, 1H), 2.82 (d, J=13.5 Hz, 1H), 2.91 (t, J=7.2 Hz, 2H), 3.86 (t, J=7.2 Hz, 2H), 5.78 (s, 1H), 7.17-7.31 (m, 5H).

Example 22. 9-(phenethoxymethylene)cyclododeca-1,5-diene

The title compound was prepared starting from cyclododeca-4,8-dien-1-one (mixture of E,E-, E,Z- and Z/E-isomers). It was isolated by short-path distillation (bp 172° C., 30 mTorr) from the crude reaction mixture as a colorless oil in 83% yield (mixture of stereoisomers) from the intermediate methyl enol ether.

$^1$H NMR (CDCl$_3$, 500 MHz, isomer mixture): δ 1.30-1.61 (m, 2H), 1.80-2.23 (m, 12H), 2.87-2.96 (overlapping triplets, 2H), 3.82-3.94 (overlapping triplets, 2H), 5.06-5.57 (m 4H), 5.75, 5.77, 5.81, 5.84, 5.89 (singlets, 1H), 7.16-7.32 (m, 5H).

Example 23. (1 SR,4RS,4aSR,8aRS)-6-methyl-7-(phenethoxymethylene)decahydro-1,4-methanonaphthalene The title compound was prepared starting from (1RS,4SR, 4aRS,8aSR)-7-methyloctahydro-1,4-methanonaphthalen-6 (2H)-one. It was isolated by short-path distillation (bp 165-170° C., 15 mTorr) from the crude reaction mixture followed by Kugelrohr distillation (oven 150° C., 25 mTorr) as a pale yellow oil in 58% yield (mixture of four stereoisomers) from the intermediate methyl enol ether.

$^1$H NMR (CDCl$_3$, 500 MHz, isomer mixture): δ 0.97, 0.98, 1.03, 1.07 (doublets, J=6.9, 6.7, 7.2, 7.1 Hz, 3H), 1.00 (m, 2H), 1.10-1.24 (m, 2H), 1.28-1.60 (m, 7H), 1.61-1.76, 1.77-1.92 (m, 3H), 2.13, 2.41, 2.54, 2.67 (m, 1H), 2.91 (t, J=7.2 Hz, 2H), 3.80-3.90 (overlapping triplets, 2H), 5.79, 5.84, 5.87 (singlets, 1H), 7.17-7.30 (m, 5H).

Example 24. (2-(((2RS,5SR)-2-isopropyl-5-methyl-cyclohexylidene)methoxy)ethyl)benzene The title compound was prepared starting from 2-isopropyl-5-methylcyclohexan-1-one (80% trans isomer). It was isolated by short-path distillation (bp 130-135° C., 15 mTorr) from the crude reaction mixture as a pale yellow oil in 72% yield from the intermediate methyl enol ether (E/Z=60:40).

$^1$H NMR (CDCl$_3$, 500 MHz, isomer mixture): δ 0.77, 0.89 (triplets, J=6.7, 7.0 Hz, 3H), 0.87, 0.90 (triplets, J=6.7, 6.7 Hz, 6H), 0.93, 1.09, 1.18, 1.28 (m, 2H), [1.45-1.97 (m, 2H), 2.22 (dd, J=13.5, 5.3 Hz), 2.28 (dt, J=10.4, 3.8 Hz), 2.42 (dd, J=12.8, 3.8 Hz) (7H)], 2.85-2.94 (m, 2H), 3.78-3.92 (m, 2H), [5.78 (d, J=1.4 Hz), 5.80 (s) (1H)], 7.18-7.33 (m, 5H).

Example 25. (2-((2-(2-((R)-4-methylcyclohex-3-en-1-yl)propyl)cyclopentylidene)methoxy)ethyl)benzene The title compound was prepared starting from 2-(2-((R)-4-methylcyclohex-3-en-1-yl)propyl)cyclopentan-1-one (4 diastereomers). It was isolated by Kugelrohr distillation (oven 220-225° C., 20 mTorr) from the crude reaction mixture as a colorless oil in 70% yield (mixture of stereoisomers) from the intermediate methyl enol ether.

$^1$H NMR (CDCl$_3$, 500 MHz, isomer mixture): δ 0.80-0.88 (overlapping doublets, 3H), 0.91-2.46 (m, 17H), 1.64 (s, 3H), 2.90, 2.91 (overlapping triplets, J=7.2 Hz, 2H), 3.82-3.92 and 3.89 (m and t, J=7.2 Hz, 2H), 5.38 (br s, 1H), 5.83-5.87, 5.91-5.94 (br overlapping singlets, 1H), 7.17-7.30 (m, 5H).

Example 26. (2-((2-pentylcyclopentylidene)methoxy)ethyl)benzene

The title compound was prepared starting from 2-pentylcyclopentan-1-one. It was isolated by Kugelrohr distillation (oven 160-180° C., 20 mTorr) from the crude reaction mixture as a colorless oil in 88% yield from the intermediate methyl enol ether (E/Z=62:38).

$^1$H NMR (CDCl$_3$, 500 MHz, E-isomer): δ 0.89 (t, J=6.9 Hz, 3H), 1.09-1.39 (m, 8H), 1.39-1.56 (m, 2H), 1.60-1.75 (m, 2H), 1.75-1.86 (m, 1H), 2.07-2.17 (m, 1H), 2.28-2.36 (m, 1H), 2.91 (t, J=7.2 Hz, 2H), 3.89 (t, J=7.2 Hz, 2H), 5.87 (q, J=2.2 Hz, 1H), 7.16-7.33 (m, 5H).

Example 27. (2-((2-heptylcyclopentylidene)methoxy)ethyl)benzene

The title compound was prepared starting from 2-heptylcyclopentan-1-one. It was isolated by Kugelrohr distillation (oven 195-205° C., 20 mTorr) from the crude reaction mixture as a colorless oil in 87% yield from the intermediate methyl enol ether (E/Z=62:38).

$^1$H NMR (CDCl$_3$, 500 MHz, E-isomer): δ 0.88 (t, J=6.9 Hz, 3H), 1.10-1.38 (m, 12H), 1.38-1.55 (m, 2H), 1.60-1.74 (m, 2H), 1.74-1.86 (m, 1H), 2.08-2.18 (m, 1H), 2.28-2.37 (m, 1H), 2.92 (t, J=7.2 Hz, 2H), 3.89 (t, J=7.2 Hz, 2H), 5.87 (q, J=2.1 Hz, 1H), 7.16-7.33 (m, 5H).

Example 28. (2-((2-ethyl-4,4-dimethylcyclohexylidene)methoxy)ethyl)benzene

The title compound was prepared starting from 2-ethyl-4,4-dimethylcyclohexan-1-one. It was isolated by Kugelrohr distillation (oven 140-145° C., 20 mTorr) from the crude reaction mixture as a pale yellow oil in 89% yield from the intermediate methyl enol ether (E/Z=91:9).

$^1$H NMR (CDCl$_3$, 500 MHz, E-isomer): δ 0.82 (t, J=12.1 Hz, 1H), 0.89 (s, 3H), 0.90 (t, J=7.4 Hz, 3H), 0.95 (s, 3H), 1.09-1.20 (m, 1H), 1.34-1.43 (m, 1H), 1.49-1.59 (m, 2H), 1.74 (td, J=13.5, 4.4 Hz, 1H), 1.89 (sextet, J=5.6 Hz, 1H), 2.66 (dt, J=13.8, 3.9 Hz, 1H), 2.91 (t, J=7.1 Hz, 2H), 3.87 (t, J=7.1H, 2H), 5.70 (s, 1H), 7.16-7.30 (m, 5H).

Example 29. (2-((2-ethyl-4-methylhex-1-en-1-yl)oxy)ethyl)benzene

The title compound was prepared starting from 5-methylheptan-3-one. It was isolated by short-path distillation from the crude reaction mixture as a pale yellow oil in 66% yield from the intermediate methyl enol ether (isomer ratio=58:42).

$^1$H NMR (CDCl$_3$, 500 MHz, isomer mixture): δ 0.80 (d, J=6.7 Hz, 3H), 0.86, 0.87 (triplets, J=7.4 Hz, 3H), 0.94, 0.95 (triplets, J=7.8 Hz, 3H), 1.01-1.04 (m, 1H), 1.28-1.52 (m, 2H), 1.55-1.61, 1.84-2.14 (multiplets, 4H), 2.89, 2.90 (triplets, J=7.0 Hz, 2H), 3.83, 3.86 (triplets, J=7.0 Hz, 2H), 5.74, 5.86$_{major\ isomer}$ (singlets, 1H), 7.17-7.31 (m, 5H).

2. Headspace Analysis from Fabric Softener Application

A model liquid fabric softener was prepared by mixing a TEA-esterquat (Stepantex® VL 90 A), 12.3 wt %, 10% aqueous calcium chloride, 0.4 wt %, Proxcel GXL, 0.04 wt % and deionized water, 87.2 wt %. The enol ethers (0.075 mmol) were weighed into a vial and dissolved in 0.25 mL of acetone. Liquid fabric softener (4.5 g) was added to the vial and the mixture shaken by hand to mix. Reference samples were prepared in the same manner using 0.075 mmol of each released volatile. The fabric softener samples were rinsed with deionized water into a 3 L beaker and the beaker was filled to a total volume of 1.5 L. Three, 5-g cotton swatches (ca. 12.5×12.5 cm, weight 270 g/m$^2$, item 403 from Testfabrics, West Pittston, Pa.) were added to the beaker and agitated by hand for 3 min. After an additional 2 min of standing, the swatches were removed and excess water squeezed out by hand. The cloths were hung to dry overnight (15-16 h) at rt. The swatches then were subjected to dynamic headspace analysis.

Each swatch was placed inside a thermostatted (25° C.), headspace sampling cell (about 160 mL volume). Using an air-sampling pump, a constant flow of air (200 mL/min) was drawn through the sampling cell and then through a cartridge containing 100 mg of Tenax® (the waste cartridge). Prior to entering the sample cell, the air was drawn through a plug of active charcoal and then through a saturated NaCl solution to maintain a constant relative humidity of 75%. Headspace samples were collected after 1 and 2 hours by replacing the waste cartridge with a clean Tenax® cartridge for 15 min. The cartridges were thermally desorbed with a Perkin Elmer TurboMatrix 650 thermal desorber coupled to an Agilent 6890 gas chromatograph equipped with an Agilent 5975C mass spectrometer and a Varian VF-1 ms capillary column (30 m, i.d. 0.25 mm, film 0.25 µm). The desorber parameters were: valve temperature 250° C., transfer line 250° C., purge time 1 min, desorption temperature 240° C., desorption time 5 min, desorption flow 20 mL/min, trap −30° C. to 250° C. at 40° C./sec, trap hold time 4 min, outlet split 48 mL/min, column flow 1 mL/min. The GC oven temperature profile was 60° C. (1 min) to 210° C. at 20° C./min then ramped to 250° C. (2 min). When analysing for pipol the initial oven temperature was 52° C. (2 min). The amount of each fragrance volatile collected (reported as ng/L of air) was determined using external standard calibrations of the respective chemicals. At least five acetone solutions were prepared with concentrations of the analytes ranging from 0.05 g/L to 5 g/L. The solutions were injected (0.2 µL) onto Tenax® cartridges and desorbed as described above. Each solution was analyzed in triplicate. Calibration curves were forced through the origin.

Dynamic headspace concentrations (ng/L) of perfumery raw materials obtained from line-dried cotton treated with fabric softener containing enol ether profragrances compared to their respective references (data for the 60-75 and 120-135 min headspace samples).

|  |  | 60 min sample | | 120 min sample | |
|---|---|---|---|---|---|
|  |  | profragrance | reference | profragrance | reference |
| Ex. 1 | 2-undecanone | 143 ± 11 | 3.2 ± 1.9 | 121 ± 33 | 4.6 ± 3.5 |
|  | 2-phenylethyl formate | 307 ± 27 | 0.5 ± 0.3 | 241 ± 104 | 0.4 ± 0.1 |
|  | 2-phenylethanol | 17 ± 1.4 | 8.1 ± 2.0 | 40 ± 35 | 15 ± 3.4 |
| Ex. 3 | 4-phenyl-2-butanone | 393 ± 103 | 1.2 ± 0.6 | 314 ± 57 | 1.9 ± 1.0 |
|  | 2-phenylethyl formate | 243 ± 55 | 0.3 ± 0.1 | 181 ± 11.7 | 0.3 ± 0.03 |
|  | 2-phenylethanol | 36 ± 5.9 | 14 ± 7.6 | 37 ± 5.3 | 27 ± 16 |
| Ex. 5 | 4-(2,6,6-trimethylcyclohex-1-en-1-yl)butan-2-one | 230 ± 18 | 68 ± 10 | 207 ± 38 | 86 ± 10 |
|  | 2-phenylethyl formate | 484 ± 141 | 0.4 ± 0.1 | 351 ± 120 | 0.5 ± 0.2 |
|  | 2-phenylethanol | 32 ± 1.3 | 14 ± 2.7 | 39 ± 1.4 | 24 ± 2.9 |
| Ex. 9[a] | 4-(4-methoxyphenyl)butan-2-one | 40.4 ± 10.1 | 6.1 ± 1.0 | 33.2 ± 17.4 | 4.6 ± 0.9 |
|  | 2-phenylethyl formate | 47.7 ± 17.1 | 2.2 ± 1.9 | 34.9 ± 20.2 | 1.0 ± 0.1 |
|  | 2-phenylethanol | 18.8 ± 4.9 | 14.2 ± 3.4 | 12.7 ± 7.1 | 11.4 ± 1.8 |
| Ex. 10 | 2-undecanone | 195 ± 53.1 | 2.9 ± 0.9 | 193 ± 58.0 | 4.0 ± 0.2 |
|  | 3-octyl formate | 15.5 ± 0.5 | 5.3 ± 4.5 | 20.0 ± 2.4 | 10.8 ± 0.5 |
|  | 3-octanol | 51.7 ± 3.11 | 1.9 ± 1.7 | 68.4 ± 9.6 | 1.9 ± 0.6 |
| Ex. 16 | 2-undecanone | 56.9 ± 11.3 | 1.4 ± 0.5 | 69.6 ± 10.6 | 1.2 ± 0.5 |
|  | (Z)-3-hexen-1-yl formate | 12.3 ± 1.2 | <1 | 12.1 ± 2.1 | 0.3 ± 0.02 |
|  | (Z)-3-hexen-1-ol | 35.4 ± 1.5 | <1 | 44.6 ± 13.2 | 0.8 ± 0.1 |
| Ex. 17 | 2-decanone | 45.5 ± 3.4 | 1.1 ± 0.8 | 43.9 ± 4.2 | 1.3 ± 1.3 |
|  | 2-phenylethyl formate | 83.7 ± 24.6 | 2.0 ± 0.5 | 59.5 ± 20.0 | 1.6 ± 0.9 |
|  | 2-phenylethanol | 21.8 ± 7.3 | 19.2 ± 6.2 | 23.1 ± 2.6 | 22.0 ± 8.0 |
| Ex. 18 | 2-undecanone | 123 ± 28 | 2.4 ± 1.2 | 135 ± 20 | 4.3 |
|  | citronellyl formate | 63.8 ± 16.9 | 1.9 ± 0.5 | 64.5 ± 16.0 | 7.5 |
|  | citronellol | 13.9 ± 3.1 | 2.1 ± 0.5 | 22.0 ± 0.4 | 3.0 |
| Ex. 19 | 3-heptanone | 16.7 ± 1.9 | 1.1 | 15.2 ± 1.8 | 4.4 |
|  | 2-phenylethyl formate | 109 ± 44.6 | 3.3 | 93.7 ± 24.4 | 2.4 ± 0.5 |
|  | 2-phenylethanol | 20.2 ± 8.3 | 31.8 | 24.4 ± 12.6 | 48.6 ± 24.3 |
| Ex. 22[a] | cyclododeca-4,8-dien-1-one | 80.6 ± 12.5 | 4.5 ± 2.7 | 81.5 ± 17.0 | 4.1 ± 2.6 |
|  | 2-phenylethyl formate | 96.3 ± 23.1 | 0.8 ± 0.1 | 82.3 ± 24.8 | 0.8 ± 0.6 |
|  | 2-phenylethanol | 11.4 ± 1.5 | 27.6 ± 14.7 | 14.9 ± 3.3 | 32.4 ± 19.2 |
| Ex. 23[a] | 7-methyloctahydro-1,4-methanonaphthalen-6(2H)-one | 109 ± 19.5 | not det. | 106 ± 26.1 | not det. |
|  | 2-phenylethyl formate | 137 ± 58.0 | 1.0 ± 0.1 | 89.2 ± 28.3 | 0.95 ± 0.7 |
|  | 2-phenylethanol | 44.1 ± 9.6 | 31.1 ± 16.5 | 48.6 ± 16.6 | 37.6 ± 20.8 |
| Ex. 26 | 2-pentylcyclopentanone | 35.9 ± 14.6 | 0.8 ± 0.1 | 39.5 ± 19.6 | 0.7 ± 0.5 |
|  | 2-phenylethyl formate | 82.3 ± 34.6 | 2.3 ± 0.9 | 80.4 ± 43.7 | 1.6 ± 0.9 |
|  | 2-phenylethanol | 29.9 ± 2.1 | 9.7 ± 4.2 | 35.5 ± 6.6 | 20.8 ± 5.1 |
| Ex. 27 | 2-heptylcyclopentanone | 76.9 ± 13.2 | 12.9 ± 6.95 | 137 ± 29.9 | 20.9 ± 8.9 |
|  | 2-phenylethyl formate | 49.7 ± 17.2 | 0.4 | 51.3 ± 19.3 | not det. |
|  | 2-phenylethanol | 15.6 ± 1.9 | 20.8 ± 11.0 | 32.5 ± 15.0 | 22.9 ± 4.8 |

[a] Headspace sampling cell thermostatted at 30° C.

3. Olfactive Evaluation with a Leave-on Hair Conditioner

A model rinse-off hair conditioner was prepared in a generally known manner with the following composition (weight %):

| Deionized water | 95.50% |
|---|---|
| Salcare SC 91 (origin: BASF) | 1.00% |
| Aculyn ™ 46 (origin: Dow) | 1.00% |
| Wacker-Belsil ® DMS 6038 (origin: Wacker) | 0.50% |
| Phenonip ™ (origin: Clariant) | 0.50% |
| Mirasil ® ADM-E (origin: Elkem) | 1.50% |

A 25% enol ether solution in isopropyl myristate or a 25% enol ether solution in acetone was dispersed in a leave-on hair conditioner to provide samples containing 0.15 wt % or 0.25 wt % of the precursor, respectively. Reference samples containing an equimolar level of the expected ketone and formate ester were prepared in the same way. The samples were left macerating at room temperature for one day. The hair swatches (10 g) were rinsed under warm tap water (370) for 30 s then gently combed to straighten the hair. The hair conditioner samples (1 g) were each applied to a swatch and massaged into the hair to disperse thoroughly. The swatches were hung and allowed to dry at room temperature. They were olfactively evaluated by a panel for odor intensity after 6 and 24 h. Panelists were asked to rate the perceived odor intensity on a scale ranging from 1 (imperceptible) to 7 (very intense). The data obtained from the panel evaluations are summarized in the below table.

| Tested molecule (wt % in conditioner) | Mean Odor Intensity (# of panelists) | |
|---|---|---|
|  | 6 hours | 24 hours |
| Reference materials |  |  |
| Example 1 (0.25%) | 3.4 (17) | 4.3 (13) |
| 2-undecanone 2-phenylethyl formate | 2.4 (17) | 2.5 (13) |
| Example 9 (0.25%) | 4.1 (17) | 4.5 (13) |
| 4-(4-methoxyphenyl)butan-2-one 2-phenylethyl formate | 2.2 (17) | 2.1 (13) |

-continued

| Tested molecule (wt % in conditioner) | Mean Odor Intensity (# of panelists) | |
|---|---|---|
| Reference materials | 6 hours | 24 hours |
| Example 1 (0.15%) | 4.5 (19) | 4.0 (19) |
| 2-undecanone 2-phenylethyl formate | 2.0 (19) | 1.4 (19) |
| Example 9 (0.15%) | 4.8 (20) | 4.8 (21) |
| 4-(4-methoxyphenyl)butan-2-one 2-phenylethyl formate | 2.6 (20) | 2.0 (21) |

These data show that the compounds of formula (I) produced a higher odor intensity on hair than the corresponding reference samples at both 6 h and 24 h after application from a leave-on hair conditioner. This demonstrates that the compounds of the invention produced the desired slow-release effect.

4. Olfactive Evaluation with a Rinse-Off Hair Conditioner

A model rinse-off hair conditioner was prepared in a generally known manner with following composition (weight %)

| Deionized water | 92.54% |
|---|---|
| Chlorhexidine dihydrochloride | 0.05% |
| Natrosol ® 250 H (origin: Hercules) | 1.00% |
| Dehyquart ® C 4046 (origin: Cognis) | 0.20% |
| Mirasil ® ADM-E (origin: Rhodia) | 1.20% |
| Genamin ® KDM (origin: Clariant) | 1.00% |
| Crodamol ® SS (origin: Croda) | 0.50% |
| Crodacol ® C90 (origin: Croda) | 3.01% |
| Myristyl alcohol (origin: Aldrich) | 0.20% |
| Nipagin ® M (origin: Nipa) | 0.30% |

A 25% enol ether solution in isopropyl myrisate was dispersed in a rinse-off hair condition to provide samples containing either 0.25 or 0.15 wt % of the precursor. Reference samples containing an equimolar level of the expected ketone and formate ester were prepared in the same way. The samples were left macerating at room temperature for one day. Hair swatches (10 g) were wetted with warm tap water (about 370) and washed with an unperfumed milky shampoo. The shampoo (1 mL) was applied with a syringe along the length of each hair swatch. The swatches were massaged with fingertips for 30 s to distribute the shampoo and develop a good lather. They were rinsed with warm tap water for 30 s and the excess water gently squeezed out. The rinse-off conditioner (1.0 g) was applied along the hair swatch and gently massaged into the hair for 1 min. The swatch was then dipped in a 2-L beaker of warm tap water and moved up and down three times and then side-to-side three times. It then was rinsed for 30 s with tap water while detangling the hair with fingertips. After gently squeezing out excess water, the swatches were hung and allowed to dry at room temperature. The swatches were olfactively evaluated by a panel for odor intensity after 6 and 24 h. Panelists were asked to rate the perceived odor intensity on a scale ranging from 1 (imperceptible) to 7 (very intense). The data obtained from the panel evaluations are summarized in the below table.

| Tested molecule (wt % in conditioner) | Mean Odor Intensity (# of panelists) | |
|---|---|---|
| Reference materials | 6 hours | 24 hours |
| Example 1 (0.25%) | 4.0 (18) | 4.5 (17) |
| 2-undecanone 2-phenylethyl formate | 2.0 (18) | 1.8 (17) |
| Example 1 (0.15%) | 4.5 (20) | 3.1 (18) |
| 2-undecanone 2-phenylethyl formate | 1.7 (20) | 1.6 (18) |
| Example 9 (0.25%) | 3.9 (19) | 3.8 (18) |
| 4-(4-methoxyphenyl)butan-2-one 2-phenylethyl formate | 2.8 (19) | 1.9 (18) |
| Example 9 (0.15%) | 4.4 (24) | 3.6 (15) |
| 4-(4-methoxyphenyl)butan-2-one 2-phenylethyl formate | 2.2 (24) | 1.7 (15) |

These data show that the compounds of formula (I) produced a higher odor intensity on hair than the corresponding reference samples at both 6 h and 24 h after application from a rinse-off hair conditioner. This demonstrates that the compounds of the invention produced the desired slow-release effect.

5. Olfactive Evaluation in Pearly Shampoo

A model pearly shampoo was prepared in a generally known manner with following composition (weight %)

| Deionized water | 46.27% |
|---|---|
| EDETA B Powder (origin: BASF) | 0.05% |
| Jaguar C14 S ® (origin: Rhodia) | 0.05% |
| UCare ™ Polymer JR-400 (origin: Dow) | 0.075% |
| 10% NaOH solution | 0.30% |
| Sulfetal LA B-E (origin: Z&H Handel) | 34.00% |
| Zetesol LA ® (origin: Z&H Handel) | 9.25% |
| Tego ® Betaine F 50 (origin: Evonik) | 2.00% |
| Xiameter ® MEM-1691 (origin: Dow Corning) | 2.50% |
| Cetyl alcohol | 1.20% |
| Comperlan 100 (origin: BTC Speciality Techn.) | 1.50% |
| Cutina ® AGS (origin: BASF) | 2.00% |
| Kathon ™ CG (origin: Dow) | 0.10% |
| Panthenol 75% (origin: BASF) | 0.10% |
| Sodium Chloride 25% | 0.60% |

A 25% enol ether solution in isopropyl myrisate was dispersed in a pearly shampoo to provide samples containing 0.15 wt % of the precursor. A reference sample containing an equimolar level of the expected ketone and formate ester was prepared in the same way. The samples were left macerating at room temperature for one day. Hair swatches (10 g) were wetted with warm tap water (about 370) and washed with milky shampoo. The shampoo (1 gram) was applied with a syringe along the length of each hair swatch. The swatches were massaged with fingertips for 30 s to distribute the shampoo and develop a good lather. They were rinsed with warm tap water for 30 s and the excess water gently squeezed out. The swatches then were washed again with the pearly shampoo for 30 sec and rinsed for 30 sec with warm tap water. After gently squeezing out excess water, the swatches were hung and allowed to dry at room temperature. The swatches were olfactively evaluated by a panel of 18-19 people for odor intensity after 6 and 24 h. Panelists were asked to rate the perceived odor intensity on a scale ranging from 1 (imperceptible) to 7 (very intense). The data obtained from the panel evaluation are summarized in the below table.

| Tested molecule (wt % in shampoo) | Mean Odor Intensity (# of panelists) | |
| --- | --- | --- |
| Reference materials | 6 hours | 24 hours |
| Example 9 (0.15%) | 2.8 (19) | 3.2 (18) |
| 4-(4-methoxyphenyl)butan-2-one 2-phenylethyl formate | 1.5 (19) | 1.3 (18) |

These data show that the compound of formula (I) produced a higher odor intensity on hair than the corresponding reference samples at both 6 h and 24 h after application from a shampoo. This demonstrates that the compounds of the invention produced the desired slow-release effect.

6. Olfactive Evaluation with an Antiperspirant/Deodorant Stick

A model deodorant was prepared in a generally known manner with following composition (weight %)

| | |
| --- | --- |
| Dow Corning 345 Fluid | 55.00% |
| Lanette ® 18 (origin: BASF) | 21.00% |
| Tegosoft ® PBE (origin: Evonik) | 2.00% |
| Cutina ® HR (origin: BASF) | 1.00% |
| Summit ® AZP-908 (origin: SummitReheis) | 20.00% |

A sample containing 0.15 wt % of an enol ether profragrance was prepared by dispersing a 15:20 mixture of the enol ether and isopropyl myristate in the molten antiperspirant composition. A reference sample containing an equimolar level of the expected ketone and formate ester was prepared in the same way. The molten samples were poured into deodorant stick molds and left macerating at room temperature for one day. An amount of 0.25 g of each sample was spread evenly on paper blotters of 4.5 cm×12 cm. The blotters were stored under ambient conditions for 6 and 24 h. The blotters were olfactively evaluated by a panel for odor intensity after 6 and 24 h. Panelists were asked to rate the perceived odor intensity on a scale ranging from 1 (imperceptible) to 7 (very intense). The data obtained from the panel evaluations are summarized in the below table.

| Tested molecule (wt % in AP/Deo stick) | Mean Odor Intensity (# of panelists) | |
| --- | --- | --- |
| Reference materials | 6 hours | 24 hours |
| Example 1 (0.15%) | 3.5 (19) | 3.2 (20) |
| 2-undecanone 2-phenylethyl formate | 1.8 (19) | 1.6 (20) |
| Example 9 (0.15%) | 3.8 (18) | 3.6 (18) |
| 4-(4-methoxyphenyl)butan-2-one 2-phenylethyl formate | 2.4 (18) | 2.0 (18) |

These data show that the compounds of formula (I) produced higher odor intensities on blotters than the corresponding reference samples 6 h after application from an antiperspirant stick. This demonstrates that the compounds of the invention produced the desired slow-release effect.

7. Olfactive Evaluation in an Eau de Toilette

A 1% solution of the enol ether in ethanol 40B and water (85:15 by weight) was prepared. A reference sample containing an equimolar level of the expected ketone and formate ester was prepared. If a mixture did not become homogeneous, both the enol ether and corresponding reference sample were sonicated in a 25° C. water bath for 10-20 min. 20 µl of each solution was applied to the center of 4.5 cm×12 cm paper blotter. The blotters were stored under ambient conditions for 3 and 6 h. The blotters were olfactively evaluated by a panel of 20-25 people for odor intensity after 6 and 24 h. Panelists were asked to rate the perceived odor intensity on a scale ranging from 1 (imperceptible) to 7 (very intense). The data obtained from the panel evaluations are summarized in the below table.

| Tested molecule (wt % in eau de toilette) | Mean Odor Intensity (# of panelists) | |
| --- | --- | --- |
| Reference materials | 3 hours | 6 hours |
| Example 1 (1%) | 3.6 (24) | 3.3 (25) |
| 2-undecanone 2-phenylethyl formate | 2.1 (24) | 1.8 (25) |
| Example 9 (1%) | 3.9 (20) | 4.2 (20) |
| 4-(4-methoxyphenyl)butan-2-one 2-phenylethyl formate | 3.6 (20) | 3.3 (20) |

These data show that the compounds of formula (I) produced higher odor intensities on blotters than the corresponding reference samples 3 h and 6 h after application from an ethanolic solution. This demonstrates that the compounds of the invention produced the desired slow-release effect.

8. Performance in Fabric Softener Application of the Inventions Compound and Compounds Disclosed in US 3004/0013779 (Comparative Example)

To compare the performance of these enol ethers as profragrances, fabric softener samples were prepared as described above by mixing 0.075 mmol of enol ether Example 1 with 0.075 mmol of either enol ether compound disclosed in US 2004/0013779 (1-ethoxydodec-1-ene and 1-butoxydodec-1-ene) and 4.5 g of the fabric softener. 1-Butoxydodec-1-ene was prepared according to Example 10 of US 2004/0013779 using dodecanal and 1-butanol as starting materials and isolated as a mixture of isomers (E/Z=44:56). As described above, cotton swatches were rinsed with the fabric softener samples, hung to dry (15-16 h) and then subjected to dynamic headspace analysis. The Table below summaries the average headspace concentrations measured for the released carbonyl compounds (2-undecanone or undecanal). In both cases the headspace concentration of 2-undecanone released by Example 1 was significantly higher than the concentration of undecanal released by comparative enol ethers 1-ethoxydodec-1-ene and 1-butoxydodec-1-ene. This shows that the enol ether of the invention performs better as a profragrance than either enol ether disclosed in US 2004/0013779. For the 60-75 min headspace samples, Example 1 released a 14-fold higher and a 3.3-fold higher concentration of 2-undecanone relative to the level of undecanal released by 1-ethoxydodec-1-ene or 1-butoxydodec-1-ene, respectively.

Dynamic headspace concentrations (ng/L) of perfumery raw materials obtained from line-dried cotton treated with fabric softener containing Example 1 and either 1-ethoxydece-1-ene or 1-butoxydodec-1-ene (data for the 60-75 and 120-135 min headspace samples and standard deviations) are summarized in the below table.

| enol ether | released carbonyl compound | headspace conc. at | |
| --- | --- | --- | --- |
| | | 60-75 min | 120-135 min |
| Example 1 | 2-undecanone | 176 ± 16.3 | 132 ± 6.4 |
| 1-ethoxydodec-1-ene | 2-undecanal | 12.4 ± 0.5 | 12.8 ± 0.7 |
| Example 1 | 2-undecanone | 139 ± 25.8 | 115 ± 12.3 |
| 1-butoxydodec-1-ene | 2-undecanal | 41.8 ± 8.9 | 35.0 ± 6.4 |

9. Rates of Hydrolysis for a Compound of the Invention and Compounds Disclosed in US 3004/0013779 A1 (Comparative Example)

The rates of hydrolysis of Example 1, 1-ethoxydodec-1-ene and 1-butoxydodec-1-ene under acidic conditions were determined (FIG. 1) as a predictor of stability in acidic consumer products. Susceptibility to acid-catalysed hydrolysis would result in loss of the enol ether and hence limit its long-term storage stability. Each enol ether was dissolved a 4:1 THF/0.1 M HCl mixture and the percent remaining over time measured relative to an internal standard following the below procedure.

Into a 15 mL vial were added 125 mg of enol ether, 60 mg of hexadecane and 10 mL of THF (purged with $N_2$ and containing 2500 ppm of BFIT). After mixing, 2 mL of this solution are removed with a volumetric pipet and used to obtain the time zero measurement. 2 mL of 0.1 M HCl are mixed with the remaining 8 mL of the THF solution. This mixture is divided into 5 mL vials (1 mL per vial). The vials are gently topped with argon and fitted with screw caps around which parafilm is wrapped. The vials are stored at room temperature until analyzed. For analyses, 2 mL of ethyl acetate is added to a vial and mixed. After phase separation, the top phase is collected and washed with saturated sodium carbonate (1 mL). Duplicate samples of the organic phase are analyzed by GC-FID. For the time zero sample, 0.5 mL of deionized water is added to the 2 mL taken from the original THF solution. 1 mL of this solution is added to a 5 mL vial and then diluted with 2 mL of ethyl acetate and mixed well. The top phase is collected. 1 mL of saturated sodium carbonate is added and mixed. Two samples of the top phase then are analyzed by GC-FID. The percent of enol ether remaining was determined by comparing the ratio of the analyte to the internal standard integrated peak areas to the ratio measured at time zero.

FIG. 1 below shows that 1-ethoxydodec-1-ene and 1-butoxydodec-1-ene both hydrolysed much faster than Example 1. After six days, only 3% and 8.8% of 1-ethoxydodec-1-ene and 1-butoxydodec-1-ene remained while 83% of Example 1 remained intact. Hence, the enol ethers described in US 2004/00137791 are predicted to be less stable in acidic consumer products such as fabric softeners. This greater hydrolytic sensitivity and hence lower stability, is overcome by the enol ethers of this invention since they have much slower rates of hydrolysis.

10. Preparation of a Liquid Detergent Comprising the Invention's Compound

TABLE 1

Composition of the liquid detergent formulation

| Ingredients | Concentration [wt %] |
| --- | --- |
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Steareth-20 Methacrylate structuring Crosspolymer[5] | 6 |
| Deionized Water | 27.4 |

TABLE 1-continued

Composition of the liquid detergent formulation

| Ingredients | Concentration [wt %] |
| --- | --- |

[1] Hostapur SAS 60; Origin: Clariant
[2] Edenor K 12-18; Origin: Cognis
[3] Genapol LA 070; Origin: Clariant
[4] Origin: Genencor International
[5] Aculyn 88; Origin: Dow Chemical The liquid detergent is prepared by adding 0.005 to 5% by weight, relative to the total weight of the liquid detergent, of one or more of compounds of examples 1 to 29 into the unperfumed liquid detergent formulation of Table 1 under gentle shaking.

11. Preparation of a Transparent Isotropic Shampoo Comprising the Invention's Compound

TABLE 2

Composition of the transparent isotropic shampoo formulation

| Phases | Ingredients | Concentration [wt %] |
| --- | --- | --- |
| A | Water deionized | 44.4 |
|   | Polyquaternium-10 [1] | 0.3 |
|   | Glycerin 85% [2] | 1 |
|   | DMDM Hydantoin [3] | 0.2 |
| B | Sodium Laureth Sulfate [4] | 28 |
|   | Cocamidopropyl Betaine [5] | 3.2 |
|   | Disodium Cocoamphodiacetate [6] | 4 |
|   | Ethoxy (20) Stearyl Alcohol [6] | 1 |
| C | Sodium Laureth Sulfate [4] | 3 |
|   | Glyceryl Laureate [7] | 0.2 |
| D | Water deionized | 1 |
|   | Sodium Methylparaben [8] | 0.1 |
| E | Sodium Chloride 10% aqueous sol. | 15 |
|   | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo is prepared by dispersed in water Polyquaternium-10. The remaining ingredients of phase A are mixed separately by addition of one after the other while mixing well after each adjunction. This pre-mix is added to the Polyquaternium-10 dispersion and mixed for another 5 min. Then, the premixed phase B and the premixed Phase C are added (Monomuls 90L-12 was heated to melt in Texapon NSO IS) while agitating. Phase D and Phase E are added while agitating. PH is adjusted with citric acid solution till pH: 5.5-6.0 leading to an unperfumed shampoo formulae.

The perfumed shampoo was prepared by adding 0.005 to 5% by weight, relative to the total weight of the shampoo, of one or more of compounds of examples 1 to 29 into the unperfumed shampoo formulation of Table 2 under gentle shaking.

12. Preparation of a Structured Shower Gel Comprising the Invention's Composition

TABLE 3

Composition of the shower gel formulation

| Ingredients | Amount (% wt) |
|---|---|
| WATER deionised | 49.350 |
| Tetrasodium EDTA [1] | 0.050 |
| Acrylates Copolymer[2] | 6.000 |
| Sodium C12-C15 Pareth Sulfate [3] | 35.000 |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The shower gel is prepared by adding 0.005 to 5% by weight, relative to the total weight of the shower gel, of one or more of compounds of examples 1 to 29 into the unperfumed shower gel formulation of Table 3 under gentle shaking.

13. Preparation of a Transparent Shower Gel Comprising the Invention's Composition

TABLE 4

Composition of the transparent shower gel formulation

| Ingredients | Concentration (% wt) |
|---|---|
| WATER deionized | 52.40 |
| Tetrasodium EDTA [1] | 0.10 |
| Sodium Benzoate | 0.50 |
| Propylene Glycol | 2.00 |
| Sodium C12-C15 Pareth Sulfate [2] | 35.00 |
| Cocamidopropyl Betaine[3] | 8.00 |
| Polyquaternium-7[4] | 0.20 |
| Citric Acid (40%) | 1.00 |
| Sodium Chloride | 0.80 |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL The transparent shower gel was prepared by adding 0.005 to 5% by weight, relative to the total weight of the shower gel, of one or more of compounds of examples 1 to 29 into the unperfumed shower gel formulation of Table 4 under gentle shaking.

14. Preparation of a Milky Shower Gel Comprising the Invention's Composition

TABLE 5

Composition of the milky shower gel formulation

| Ingredients | Concentration (% wt) |
|---|---|
| WATER deionized | 50.950 |
| Tetrasodium EDTA [1] | 0.050 |
| Sodium Benzoate | 0.500 |
| Glycerin 86% | 3.500 |
| Sodium Laureth Sulfate [2] | 27.000 |
| Polyquaternium-7[3] | 1.000 |

TABLE 5-continued

Composition of the milky shower gel formulation

| Ingredients | Concentration (% wt) |
|---|---|
| Coco-Betaine[4] | 6.000 |
| PEG-120 Methyl Glucose trioleate[5] | 1.000 |
| Citric Acid (40%) | 1.000 |
| Glycol Distearate & Laureth-4 & Cocamidopropyl Betaine[6] | 3.000 |
| Sodium Chloride 20% | 5.000 |
| PEG-40 Hydrogenated Castor Oil[7] | 1.000 |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF The transparent shower gel is prepared by adding 0.005 to 5% by weight, relative to the total weight of the shower gel, of one or more of compounds of examples 1 to 29 into the unperfumed shower gel formulation of Table 5 under gentle shaking.

The invention claimed is:

1. A method to release from a precursor compound, compounds selected from the group consisting of:

a) a ketone of formula

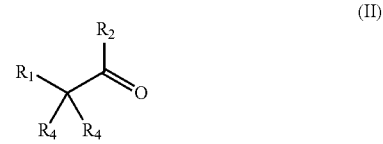

(II)

wherein $R_1$ represents a $C_{1-15}$ alkyl, $C_{2-15}$ alkenyl, $C_{3-15}$ cycloalkyl, $C_{5-15}$ cycloalkenyl or $C_{6-10}$ aryl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R_2$ represents a $C_{1-15}$ alkyl group;

$R_1$ and $R_2$, when taken together, form a $C_{5-15}$ cycloalkyl, $C_{5-15}$ cycloalkenyl, $C_{4-14}$ heterocycloalkyl or $C_{4-14}$ heterocycloalkenyl group, each optionally substituted with one or more of a $C_{1-15}$ alkyl, $C_{2-15}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid, 4-methylcyclohex-3-en-1-yl and/or $C_{1-4}$ carboxylic ester group, the heteroatom represents one or more of an oxygen;

$R_4$, each independently, represent a hydrogen or a $C_{1-5}$ alkyl group; and $R_1$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

b) a formate ester of formula

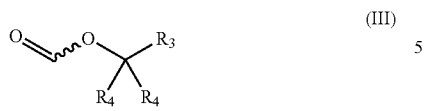
(III)

wherein $R_3$ represents a hydrogen, a $C_{1-15}$ alkyl, $C_{2-15}$ alkenyl, $C_{3-15}$ cycloalkyl or $C_{5-15}$ cycloalkenyl group, each optionally substituted with one or more a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and $R_4$ has the same meaning as defined above; and $R_3$ and $R_4$, when taken together, form a $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and c) an alcohol of formula

(IV)

wherein $R_3$ and $R_4$ have the same meaning as defined above;

wherein the precursor compound comprises a compound of formula (I)

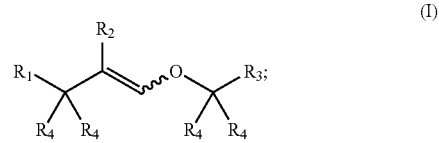
(I)

wherein $R_1$, $R_2$, $R_3$ and $R_4$ have the same meaning as defined above;

by exposing the precursor compound of formula (I) to an environment wherein the compound is oxidized.

2. The method according to claim 1, wherein $R_1$ represents a $C_{1-10}$ alkyl group optionally substituted with a $C_6$ aryl, $C_{5-7}$ cycloalkyl and/or $C_{5-7}$ cycloalkenyl group, each optionally substituted with one or more of a $C_{1-4}$ alkyl and/or $C_{1-4}$ alkoxy group.

3. The method according to claim 1, wherein $R_2$ represents a $C_{1-3}$ alkyl group.

4. The method according to claim 1, wherein $R_3$ represents a $C_{1-10}$ alkyl, $C_{3-10}$ alkenyl or $C_{5-15}$ cycloalkyl group, each optionally substituted with one or more of a $C_{1-4}$ alkyl, $C_6$ aryl and/or $C_6$ aryloxy group.

5. The method according to claim 1, wherein at least two of the compounds of formula (II), (III) or (IV) are perfuming ingredients.

6. The method according to claim 1, wherein the environment wherein the compound is oxidized is air.

7. The method according to claim 1, wherein the method provides a long-lasting odor to the environment.

* * * * *